(12) United States Patent  (10) Patent No.: US 7,767,434 B2
Chu  (45) Date of Patent: *Aug. 3, 2010

(54) ULTRASOUND-MEDIATED HIGH-SPEED BIOLOGICAL REACTION AND TISSUE PROCESSING

(75) Inventor: Wei-Sing Chu, Silver Spring, MD (US)

(73) Assignee: American Registry of Pathology, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/901,014

(22) Filed: Jul. 10, 2001

(65) Prior Publication Data

US 2001/0051343 A1  Dec. 13, 2001

Related U.S. Application Data

(62) Division of application No. 09/407,964, filed on Sep. 26, 1999, now Pat. No. 6,291,180.

(51) Int. Cl.
*C12M 1/36* (2006.01)

(52) U.S. Cl. .............. 435/286.1; 435/283.1; 435/284.1; 435/286.7

(58) Field of Classification Search .................. 382/162, 382/261; 422/20; 424/133.1, 153.1, 135.1, 424/178.1, 9.5–9.52, 153; 435/1.1–6, 287.2, 435/325, 40.5–48.5, 911–91.5; 604/20–22, 604/101

See application file for complete search history.

(56) References Cited

U.S. PATENT DOCUMENTS 3,961,097 A  6/1976  Gravlee, Jr.

4,403,509 A * 9/1983 Kretz ........................... 73/639

(Continued)

FOREIGN PATENT DOCUMENTS

WO  0117037 A1  3/2001

OTHER PUBLICATIONS

Beckstead, J.H., "A Simple Technique for Preservation of Fixation-sensitive Antigens in Paraffin-embedded Tissues", *Journal of Histochemistry and Cytochemistry*, 1994; 42(8):1127-1134.

(Continued)

*Primary Examiner*—N. C. Yang
(74) *Attorney, Agent, or Firm*—Rothwell, Figg, Ernst & Manbeck p.c.

(57) ABSTRACT

Methods of fixing and processing tissue and samples on a membrane by using ultrasound radiation as a part of the method are presented. Ultrasound of a frequency in the range of 0.1-50 MHz is used and the sample or tissue receives 0.1-200 W/cm$^2$ of ultrasound intensity. The use of ultrasound allows much shorter times in the methods. Also presented are apparati comprising transducers of one or of multiple heads for producing the ultrasound radiation and further comprising a central processing unit and optionally comprising one or more sensors. Sensors can include those to measure and monitor ultrasound and temperature. This monitoring system allows one to achieve accurate and optimum tissue fixation and processing without overfixation and tissue damage. The system also allows the performance of antigen-antibody reactions or nucleic acid hybridizations to be completed in a very short time while being highly specific and with a very low or no background.

24 Claims, 16 Drawing Sheets

U.S. PATENT DOCUMENTS

| | | | |
|---|---|---|---|
| 4,615,984 A | | 10/1986 | Stoker |
| 4,839,194 A | | 6/1989 | Malluche et al. |
| 4,891,239 A | | 1/1990 | Dudley et al. |
| 4,961,860 A | | 10/1990 | Masri |
| 4,983,523 A | * | 1/1991 | Li et al. .................... 435/173.7 |
| 5,011,296 A | * | 4/1991 | Bartosiak et al. ............ 374/131 |
| 5,089,288 A | | 2/1992 | Berger |
| 5,105,392 A | * | 4/1992 | Stringer et al. ................ 367/99 |
| 5,164,094 A | | 11/1992 | Stuckart |
| 5,197,475 A | * | 3/1993 | Antich et al. ............... 600/437 |
| 5,284,144 A | * | 2/1994 | Delannoy et al. ........... 600/412 |
| 5,639,423 A | * | 6/1997 | Northrup et al. .............. 422/50 |
| 5,665,141 A | * | 9/1997 | Vago ............................. 95/30 |
| 5,800,350 A | * | 9/1998 | Coppleson et al. ......... 600/372 |
| 5,853,994 A | | 12/1998 | Gopinathan et al. |
| 5,913,826 A | * | 6/1999 | Blank .......................... 600/500 |
| 5,941,825 A | * | 8/1999 | Lang et al. .................. 600/449 |
| 5,944,665 A | * | 8/1999 | Iino et al. .................... 600/437 |
| 5,958,341 A | * | 9/1999 | Chu ............................. 422/99 |
| 5,958,371 A | * | 9/1999 | Lanza et al. ............... 424/1.21 |
| 5,984,881 A | * | 11/1999 | Ishibashi et al. ................ 601/2 |
| 6,168,948 B1 | * | 1/2001 | Anderson et al. ........ 435/287.2 |
| 6,176,842 B1 | * | 1/2001 | Tachibana et al. ............. 604/22 |
| 6,188,162 B1 | | 2/2001 | Vennerbeck |
| 6,197,595 B1 | * | 3/2001 | Anderson et al. ........... 436/180 |
| 6,222,305 B1 | | 4/2001 | Beck et al. |
| 6,383,742 B1 | * | 5/2002 | Drmanac et al. ................ 435/6 |
| 6,401,267 B1 | * | 6/2002 | Drmanac ........................ 4/356 |
| 6,431,908 B1 | | 8/2002 | Beck et al. |
| 6,524,795 B1 | * | 2/2003 | Francis et al. ................... 435/6 |
| 6,904,921 B2 | | 6/2005 | Beck et al. |
| 7,105,985 B2 | | 9/2006 | Beck et al. |
| 7,145,286 B2 | | 12/2006 | Beck et al. |
| 7,262,022 B2 | * | 8/2007 | Chu .......................... 435/40.5 |
| 2007/0072258 A1 | * | 3/2007 | Chu .......................... 435/40.5 |

OTHER PUBLICATIONS

Boon, M.E., et al., "Microwave irradiation of human brain tissue: production of microscopic slides within one day", *J. Clin. Path.*, 1988; 41:590-593.

Chen, R., et al. "Ultrasound-Accelerated Immunoassay, as Exemplified by Enzyme Immunoassay of Choriogonadotropin", *Clinical Chemistry*, 1984; 30(9):1446-1450.

Grundy, M.A., et al. "Increased sensitivity of diagnostic latex agglutination tests in an ultrasonic standing wave field", *Journal of Immunological Methods*, 1994; 176:169-177.

Jenkins, P., et al. "Detection of meningitis antigens in buffer and body fluids by ultrasound-enhanced particle agglutination", *Journal of Immunological Methods*, 1997; 205:191-200.

Jepras, R.I., et al. "Agglutination of *Legionella pneumophila* by antiserum is accelerated in an ultrasonic standing wave", *Journal of Immunological Methods*, 1989; 120:201-205.

King, J.A.C. and Hossler, F.E. "The gill arch of the striped bass, *Morone saxatilis*. III. Morphology of the basal lamina as revealed by various ultrasonic microdissection procedures", *J. Submicrosc. Cytol. Pathol.*, 1988; 20(2):371-377.

Kondo, T. et al. "Damage in DNA Irradiated with 1.2 MHz Ultrasound and Its Effect on Template Activity of DNA for RNA Synthesis", *Radiation Research*, 1985; 104:284-292.

Kost, J., et al. "Enhanced Protein Blotting from PhastGel Media to Membranes by Irradiation of Low-Intensity Ultrasound", *Analytical Biochemistry*, 1994; 216:27-32.

Leong, A.S-Y "Microwave Fixation and Rapid Processing in a Large Throughput Histopathology Laboratory", *Pathology*, 1991; 23:271-273.

Login, G.R., et al. "Rapid Microwave Fixation of Human Tissues for Light Microscopic Immunoperoxidase Identification of Diagnostically Useful Antigens", *Laboratory Investigation*, 1987; 57(5):585-591.

Matsuta, M., et al. "Applications of DNA Flow Cytometry and Fluorescence In situ Hybridization Using a Chromosome-specific DNA Probe on Paraffin-embedded Tissue Sections of Primary Malignant Melanomas", *Journal of Dermatology*, 1994; 21:14-19.

Nishimura, R., et al. "Improved Lipid Visualization with a Modified Osmium Tetroxide Method Using Ultrasonic Treatment and Intensification with Imidazole or Triazole", *Biotechnic & Histochemistry*, 1995; 70(1):28-32.

Obertyshev, V.G. "Ultrasonic express paraffin handling of histological specimens", *Sud Med Ekspert*, 1987; 30(4):56-58 (with 2 pp. translation and 1 p. PubMed).

Podkletnova, I. and Alho, H. "Ultrasound-amplified Immunohistochemistry", *Journal of Histochemistry and Cytochemistry*, 1993; 41(1):51-56.

Sinisterra, J.V. "Application of ultrasound to biotechnology: an overview", *Ultrasonics*, 1992; 30(3):180-185.

Williams, J.H., et al. "Tissue preparation for immunocytochemistry", *J. Clin. Pathol.*, 1997; 50:422-428.

\* cited by examiner

ULTRASOUND-MEDIATED HIGH-SPEED BIOLOGICAL REACTION AND TISSUE PROCESSING

CROSS REFERENCE TO RELATED APPLICATIONS

This application is a divisional of Ser. No. 09/407,964, filed 29 Sep. 1999, now allowed, to which priority is claimed and which is incorporated herein by reference.

BACKGROUND OF THE INVENTION

The process of fixation forms the foundation for the preparation of tissue sections. It prevents or arrests autolysis and putrefaction, coagulates and stabilizes soluble and structural proteins, fortifies the tissues against the deleterious effects of subsequent processing and facilitates staining. Current methods of fixation rely on chemical agents, the most widely used being formaldehyde. Although autolysis is known to be retarded by cold and almost inhibited by heating to 60° C. (Drury and Wallington, 1980), heat as a form of tissue fixation has not been exploited in the diagnostic laboratory.

The use of routinely fixed, paraffin-embedded tissue sections for immunohistochemistry staining permits localization of a wide variety of antigens while retaining excellent morphologic detail. However, most chemical fixatives produce denaturation or masking of many antigens and degradation of RNA and DNA. In fact for some antigens, treatment of fixed tissue sections with proteases is required for their demonstration (Brandzaeg, 1982, Taylor, 1986). Furthermore, the introduction of antigen retrieval by heating tissue sections in a microwave oven (Shi et al., 1991) or pressure cooker (Norton et al., 1994: Miller et al., 1995) before immunostaining has been a major breakthrough in improving a result of no or weak immunoreactivity, particularly in suboptimally prepared tissue. However, while the optimal time for fixation varies with the chemical agent employed, this generally takes hours, approximately a day, to accomplish.

Fixative type and fixation time are known to influence 1) the preservation of tissue morphology (Baker, 1959), 2) the preservation of protein antigens for IHC (Williams et al., 1997), and 3) the preservation of nucleic acids for IHC (Weiss and Chen, 1991; Nuovo and Richart, 1989) and PCR (Ben-ezra et al., 1991). It is fortunate that formalin was found to be the best fixative for meeting these three criteria, as this is the fixative most commonly used in routine tissue fixation (Weiss and Chen. 1991; Williams et al., 1997: Nuovo and Richart. 1989).

Increasing the speed and reducing the time of fixation have been investigated using treatments of cold, heat, vacuum, microwave, ultrasound, and microwave combined with ultrasound. Tissues have been microwave irradiated for less than 10 seconds in the presence of chemical cross-linking agents (final solution temperature of 45-70° C.) (Login and Dvorak, 1985; Login et al., 1987). These MW fixation methods used heat to Pasteurize the tissue rather than to fix the tissue. The 10 seconds was not enough time to allow even penetration and complete reaction with the tissues. Also, 70° C. is not hot enough to inhibit all enzymes such as RNases (Sambrook et al., 1989). Furthermore, Azumi and Battifora reported that the improvement seen in antigen preservation in MW fixed tissues was not due to the microwave irradiation per se but rather to the graded alcohol dehydration steps in the tissue processor (Azumi et al. 1990). The exact amount of MW energy received by tissue was very difficult to control (Login and Dvorak. 1985; Azumi et al., 1990). Therapeutic ultrasound (800-880 kHz frequency and 1.4-2 W/cm$^2$ intensity) did not significantly improve the quality and time of fixation (Drakhli, 1967; Botsman and Bobrova, 1968; Obertyshev, 1987; Rozenberg, 1991) even when combined with MW energy (Shmurun, 1992). Cleaning ultrasound (destructive low frequency 40 kHz) was also used with MW. Disruptions, fissures and cracks of tissues treated for only 3 seconds with ultrasound irradiation (X 45 cycles) were observed when the specimens mere examined by light microscopy (Yasuda et al., 1992). Our findings are the same as those reports that low frequency ultrasound exposure can lead to destruction of cell and tissue structure. This indicates that the safety range of low frequency ultrasound is relatively narrow.

In the past decade, molecular pathology has been rapidly developed by using new techniques such as immunohistochemistry (IHC), in situ hybridization (ISH), fluorescent in situ hybridization (FISH), polymerase chain reaction (PCR), reverse transcription (RT)-PCR, and in situ-PCR. The most advanced techniques such as laser capture microdissection (LCM) (Emmert-Buck et al., 1996; Bonner et al., 1997; Fend et al., 1999a; Fend et al., 1999b). cDNA (Schena et al., 1995; DeRisi et al., 1996) and tissue microarrays (Kononen et al. (1998) have been developed for research and diagnosis of molecular pathology. Many genes and signaling pathways controlling cell proliferation, death and differentiation, as well as genomic integrity, have been measured by these techniques in a single experiment, revealing many, new, potentially important cancer genes. However, the tissue blocks or sections used for analysis of molecular information of LCM and tissue microarray techniques have not fitted well with the classic method of tissue fixation—formalin fixed paraffin embedded (FFPE) tissue, which has provided the best morphology for pathologists throughout this century (Fend et al., 1999; Goldsworthy et al., 1999).

FFPE tissues have been extensively studied during the last two decades for molecular biology and molecular pathology. There have been many breakthroughs in these areas such as success in isolating the 1918 "Spanish" influenza virus RNA from an 80 year old FFPE tissue block (Taubenferger et al., 1997). However, there are many drawbacks in using FFPE tissue for molecular pathology, such as inconsistency in fixation condition, antigen masking, and RNA/DNA degradation. Even using the advanced microwave-antigen retrieval method (Shi et al., 1991), several CD markers have not worked with FFPE tissues, and the average length of RT-PCR products from FFPE tissues is 200 bp (Fend et al., 1999a: Ben-ezra et al., 1991: Foss et al., 1994: Krafft et al., 1997). All these drawbacks limit the use of LCM and tissue microarray techniques with FFPE tissues (Fend et al., 1999a; Goldsworthy et al., 1999).

Six to eighteen hours are required for routine fixation of surgical tissue specimens Eight to fourteen hours are required for tissue processing. Additional times are required for embedding, sectioning, staining, and coverslipping of the specimen. A method which simultaneously permits rapid tissue fixation and processing, excellent morphologic detail, antigen preservation, and less RNA/DNA degradation would, therefore, be highly desirable in this molecular pathology era.

For the past three decades, microwave (MW) energy has sometimes been used for rapid tissue fixation (Mayers, 1970: Bernard, 1974: Login, 1978) and tissue processing (Boon et al., 1986) for light and electron microscopy. In the late 60's to early 90's, several Russian groups described a method in which therapeutic ultrasound (US) energy was used for tissue fixation and processing for light microscopy (Drakhli, 1967: Botsman and Bobrova, 1968: Obertyshev, 1987: Rozenberg, 1991) and for electron microscopy (Polonyi et al., 1984; Robb et al., 1991). MW energy combined with US energy was used in conjunction with chemical cross-linking agents to fix and process tissues for light (Shmurun, 1992) and for electron microscopy (Yasuda et al., 1992) at the same time. However, these technologies have not been successfully adopted in clinical diagnostic laboratories and controversial observations of these techniques have been reported (Azumi et al., 1990, Login et al., 1991: Azumi et al., 1991).

This invention relates to a method and apparatus for processing tissue samples or other biological samples for a wide variety of purposes. Tissue samples are analyzed for many purposes using a variety of different assays. Pathologists often use histochemistry or immunocytochemistry for analyzing tissue samples, molecular biologists may perform in situ hybridization or in situ polymerase chain reactions on tissue samples, etc. Often the sample to be analyzed will be frozen or embedded in paraffin and mounted on a microscope slide. A typical immunocytochemistry assay requires a series of many steps. These include: obtaining a tissue sample such as from a biopsy, fixing the tissue in formalin, processing the tissue overnight, embedding the tissue in paraffin cutting serial sections and mounting on microscope slides and drying. These steps are followed by steps to deparaffinize (treatments in xylene, ethanol and water), and finally the reaction can be performed on the tissue which has been mounted on the slide. Typically a series of solutions including reagents such as antibodies, enzymes, stains, etc., is dropped onto the slide, incubated, and washed off. Finally the sample may be viewed under the microscope. Clearly there are many individual steps involved and each step takes time. The current invention shortens the time for each step to be completed, and therefore shortens the time for the analysis of the tissue sample.

At present, two procedures are generally used in preparing specimens of tissue for microscopic examination. In one procedure a specimen is frozen, cut and mounted on a slide in an elapsed time of about 15 minutes. This so-called "frozen-section" procedure has the advantage of enabling a rapid histological diagnosis to be made from the specimen and it is frequently employed in situations where a diagnosis is necessary while a patient is on an operating table. The procedure possesses certain disadvantages in that the prepared slide does not possess the uniformity of quality of morphology prepared by other methods. Moreover, it is technically more difficult for serial sections of the same specimen to be examined by this procedure, and extreme caution must be exercised in cutting the specimen in order to ensure a sufficiently thin section and to avoid the possibility of damaging details of the specimen. The most serious objection to using the frozen section procedure is the necessity of preparing all the slides required for special stains and/or consultation and teaching purposes while the tissue is in the initial frozen state. If the tissue is thawed and refrozen for sectioning, it is severely damaged. Thus, when the frozen-section procedure is used in emergency situations, it is customary for another portion of the tissue specimen to be processed in the manner described hereinafter in order to have tissue available for additional sections if further examination becomes necessary.

In the other procedures a slide of relatively high quality of morphology is produced when a section of the specimen is mounted in a block of paraffin, however, the time required to process a specimen of tissue for mounting in paraffin is on the order of 24-48 hours as compared with the minutes required to process a specimen by the frozen-section procedure. In the preparation of paraffin slides, a specimen of tissue is immersed initially in a fixing agent. The fixed specimen is then immersed in a dehydrating agent, and afterward the specimen is immersed in a clearing agent. Finally, the cleared specimen is immersed in a bath of paraffin which impregnates the specimen and permits it to be sliced into thin sections for subsequent mounting onto slides. Because of the length of time required to prepare specimens by this process, it is customary for hospital laboratories to begin processing the specimens late in the afternoon after surgeons have obtained specimens from their patients. The processing continues through the night, and slides of the specimens are available for microscopic examination the next morning. Although the slides produced according to this procedure are of higher quality of morphology than those produced by the frozen-section technique, the length of time required to process specimens is too great to enable this procedure to be used in situations where time is of the essence.

In the conventional histopathology laboratory, specimens of tissue received from surgery or autopsy are trimmed and preserved in small containers of formaldehyde. The specimens are processed to remove water, and they are mounted in blocks of paraffin which are cut into thin sections. The thin sections are floated on water to enable them to be transferred to slides, and the sections are securely mounted on the slides when they are heated. Thereafter, the paraffin around the mounted sections is removed, and the sections are stained to ready them for microscopic examination.

The ability to obtain rapid results, for example, during an on-going surgery, permits a microscopic examination and diagnosis of a tissue sample and thus, due to this examination, enables suitable surgical steps to be taken during the initial surgery without requiring a follow-up later surgical procedure.

With the foregoing in mind, it is the primary object of the present invention to provide an improved method for preparing specimens of tissue for microscopic examination.

As a further object, the present invention provides an improved method by which tissue specimens of relatively high-quality of morphology can be processed for microscopic examination in a minimum amount of time.

The publications and other materials used herein to illuminate the background of the invention or provide additional details respecting the practice are incorporated by reference, and for convenience are respectively grouped in the appended List of References.

U.S. Pat. No. 3,961,097 teaches a method of using low frequency ultrasound (50 KHz) to reduce the time to perform biological processes such as fixing tissue and impregnating it with paraffin. This patent teaches placing the sample in a small beaker of reagent to react with the sample and then placing the small beaker into a larger beaker of water which is then irradiated with ultrasound. This method helped to limit damage to the sample from the ultrasound treatment. This varies from the instant invention which places the transducer which produces the ultrasound radiation within one inch of the sample. The instant invention uses ultrasound of a high frequency to minimize damage to the sample.

U.S. Pat. No. 5,089,288 also discusses the use of ultrasound treatment in the processing of tissue samples to impregnate them with paraffin. This method utilized a frequency range of 35-50 KHz. This is a looter frequency than the range of 100 KHz to 50 MHz employed by the instant invention. The higher frequencies of the instant invention result in less biological damage than do the lower frequencies of the prior art '288 patent.

Chen et al. (1984) studied the effect of ultrasound treatment on the rate of an immunoassay performed on a test strip and saw that the reaction was greatly accelerated in the presence of ultrasound. The ultrasound treatment was performed with an ultrasonic cleaner which had a nominal acoustic power output of 50 W at 50 KHz. Tests at various power (watts) were performed by varying the voltage to the sonicator.

Nishimura et al. (1995) teach a method for combining ultrasound treatment with a postfixation step in staining for lipid with osmium tetroxide. The exact specifications as to intensity and frequency of the ultrasound treatment are not disclosed. The ultrasonic treatment was performed using an ultrasonic cleaner. In general, ultrasonic cleaners produce a frequency of 20-50 KHz.

Yasuda et al. (1992) disclose a method for tissue fixation which includes a combination of microwave treatment as well as ultrasonic treatment. Overlapping pulses of a few seconds of microwave and ultrasound were administered for several cycles. The ultrasound generator was set at a dose of 20 $W/cm^2$ and a frequency of 40 KHz and was operated at 25 V. To decrease the occurrence of cavitation which is commonly caused by ultrasound treatment, the experiments were performed at 25 V instead of 100 V, tap water cooled to 0° C. was placed between the cup of the ultrasound generator and the plastic container that contained the tissue blocks and fixative, in order to make the fixative cool and to make three layers (water, plastic and fixative) so that the ultrasound energy would be reduced, and saponin or NP-40 was added to the fixatives to reduce the surface tension of the tissue blocks.

Podkletnova and Alho (1993) utilized ultrasound to increase the rate of performing immunohistochemistry. Samples were placed in plastic tubes which were placed in an ultrasonic bath of cold water (12° C.) and treated with ultrasonic irradiation for 0.5, 10, 15, 20, 30 or 40 seconds. The sonicator was operated as 220V/50 Hz. 180 W input, 90 W output, and the transducer produced a 40 kHz frequency.

A publication by Polonyi et al. (1984) teaches the use of ultrasound to accelerate glutaraldehyde-osmium fixation of animal tissues. The use of medium intensities with low frequency (20 KHz) gave good results with wet tissue but damage was caused with dehydrated tissue. Consequently the authors adopted a method of using ultrasound during the fixation, washing, postfixation and saturating steps while performing the dehydrating steps without ultrasound.

A publication by Sinisterra (1992) discusses applications of ultrasound to biotechnology. It teaches that high intensity ultrasonic waves break the cells and denature enzymes. Low intensity ultrasonic waves can improve the mass transfer of reagents and products through a boundary layer.

BRIEF DESCRIPTION OF THE FIGURES

The file of this patent contains at least one drawing executed in color. Copies of this patent with color drawing(s) will be provided b the Patent and Trademark Office upon request and payment of the necessary fee.

The transducers 13 emit ultrasound radiation and the sensors 14 send the digitized information to the central processing unit 10. The tissue sample can instead be a membrane or some other type of sample which is placed into the reaction chamber 2.

Figure 8:
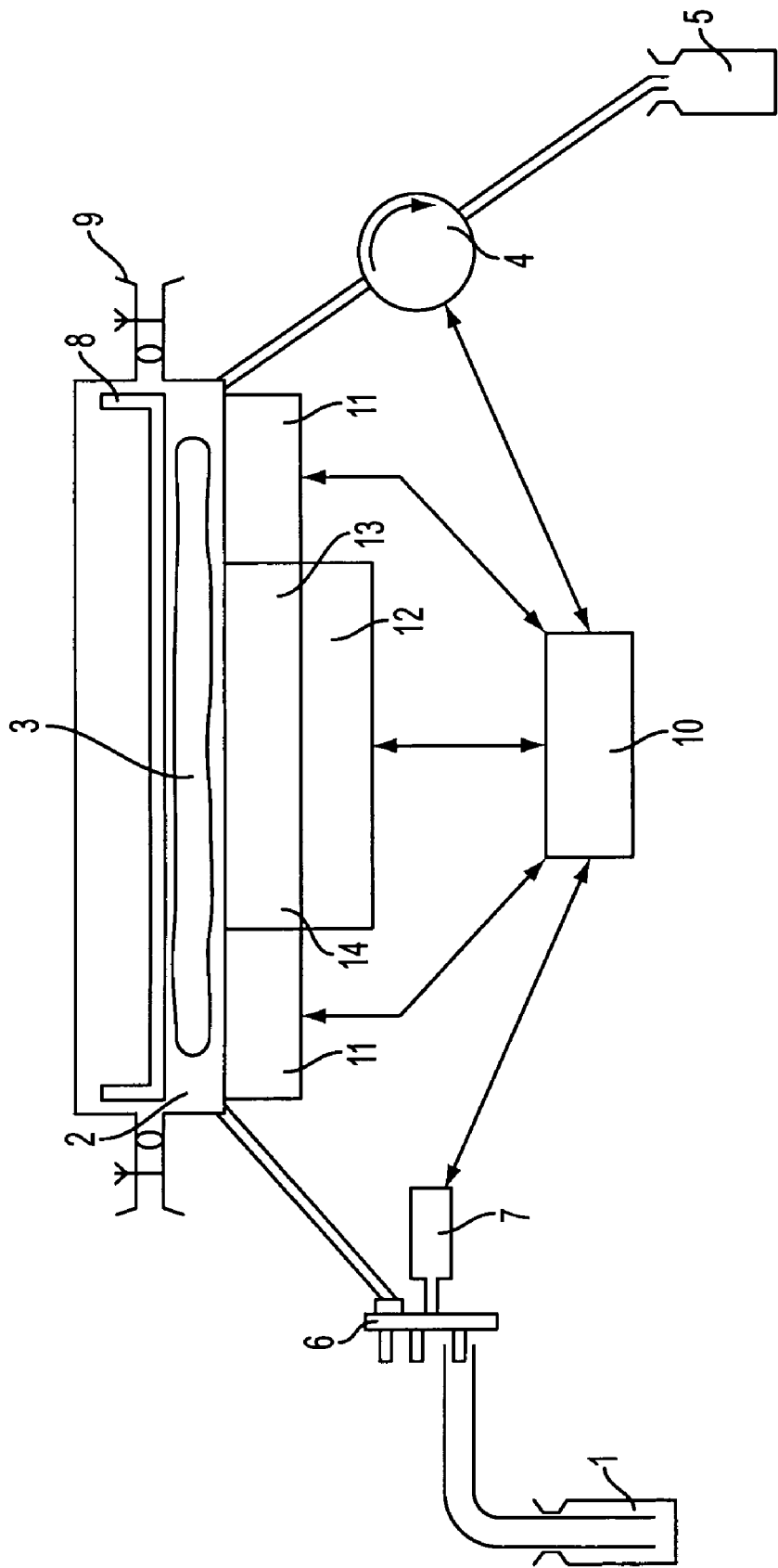
FIG. 8 illustrates an automated setup for fixing a tissue sample using ultrasound. Reagents from container 1 are pumped to a reaction chamber 2 containing sample 3. A pump 4 pumps solution from chamber 2 to a waste receptacle 5. A distributor 6 driven by motor 7 selects between different reagent containers such that different reagents can be pumped through reaction chamber 2. Tissue sample 3 is placed into the reaction chamber 2 with or without tissue cassette 8. A cover 9 encloses the chamber. A central processing unit (CPU) 10 controls motor 7 and pump 4. The CPU also controls the temperature of reaction chamber 2 by regulating a heating and cooling plate 11 in contact with the reaction chamber 2. The CPU also controls an ultrasound generator 12 and regulates the frequency and intensity of ultrasound being produced.
Figure 9:
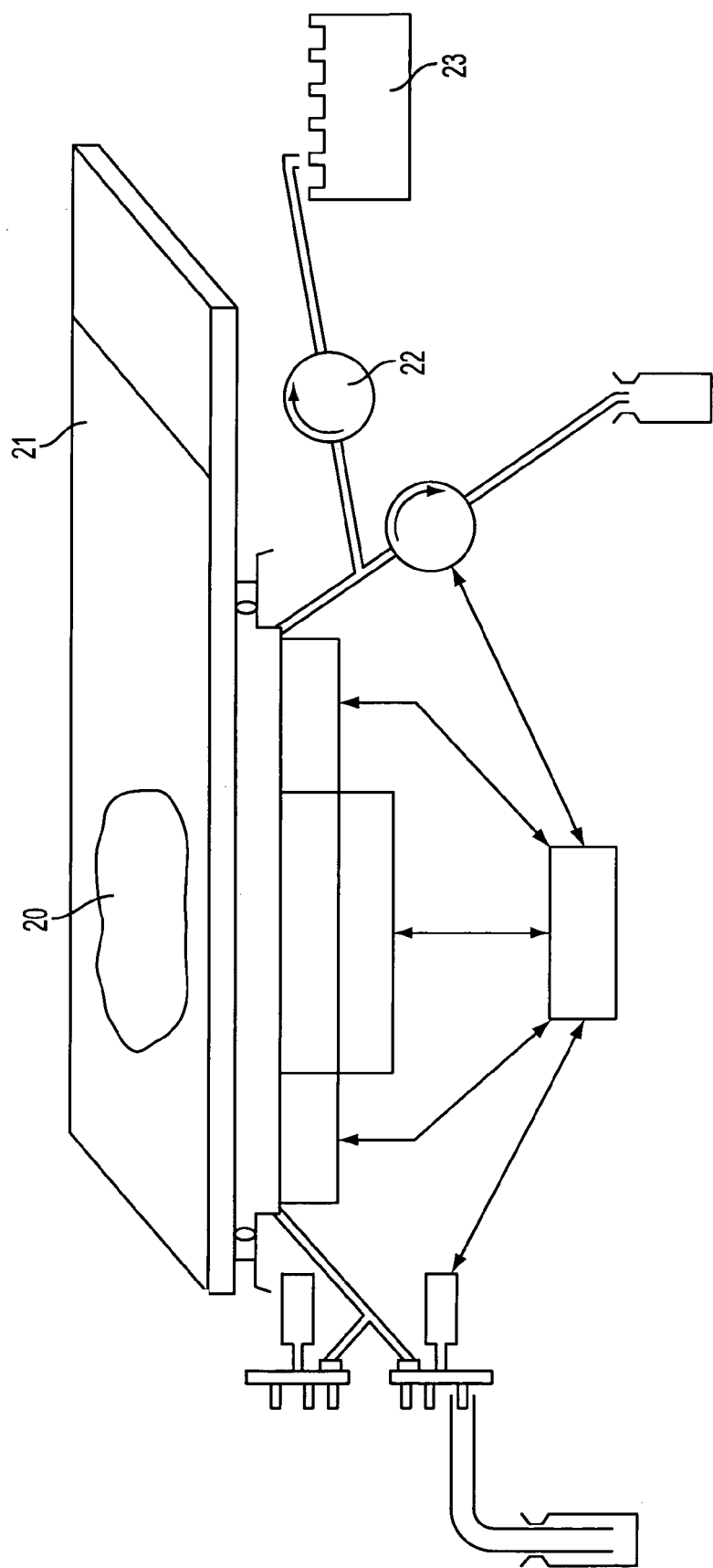

FIG. 9 illustrates a setup for performing in situ PCR hybridization with the ability to assay the reaction fluid for success of the PCR. The elements are similar to those shown in FIG. 8. Here a tissue sample 20 is mounted on a slide 21 with the tissue sample 20 facing into the reaction chamber 2 (as shown in FIG. 8). Pump 22 routes some of the solution being withdrawn from the reaction chamber 2 to a gel 23 which will be used to check for the presence of PCR products. FIG. 9 illustrates the optional use of more than one distributor.

Figure 10A:
Figure 10B:
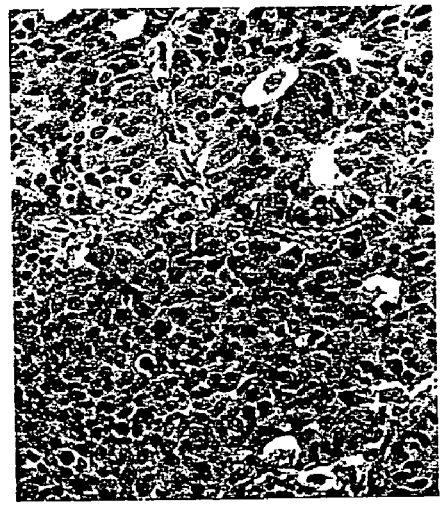

FIGS. 10A and 10B shows pictures of tissue samples which have been H&E stained using either the routine fixation and processing method (no ultrasound) or the new technique (with ultrasound).

Figure 11A:
Figure 11B:
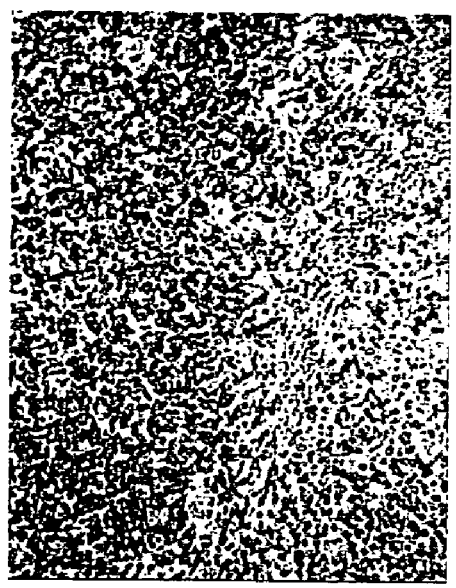

FIGS. 11A and 11B shows pictures of tissue samples which have under gone CD5 staining using the routine fixation and processing method (no ultrasound) or the new technique (with ultrasound).

Figure 12A:
Figure 12B:

FIGS. 12A and 12B shows pictures of tissue samples which have undergone in situ hybridization with poly-A mRNA using either the routine fixation and processing method (no ultrasound) or the new technique (with ultrasound).

Figure 13:
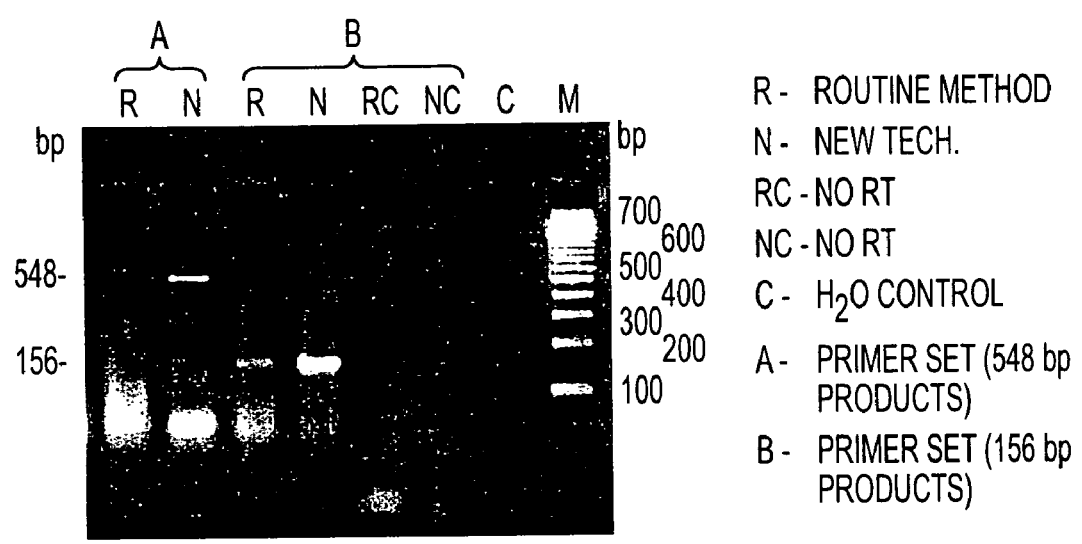

FIG. 13 shows the results of RT-PCR amplification of β-actin mRNA using the routine fixation and processing method (no ultrasound) or the new technique (with ultrasound).

SUMMARY OF THE INVENTION

The present invention is directed toward a method of decreasing the time for conducting histology or pathology study on tissue samples, e.g., biological reactions, fixation, processing, embedding, deparaffinizing, and dehydration by applying ultrasound to the tissue during these processes. The present invention discloses improved methods over the prior art. The invention is directed toward the unexpected feature of specific high frequency and high power ratings of ultrasonic treatment which result in superior results over the prior art. The high frequency, wide-band and high power ratings used are as follows and are shown graphically in FIG. 1:

1) 0.1 to 1 MHz at a low power setting;
2) 1 to 10 MHZ with a high intensity setting;
3) 10 to 50 MHZ with a low intensity setting.

It is important to understand that in the practice of the current invention more power equates to a shorter time from beginning to end for each reaction step and additionally less destruction of tissue matter. The present invention is distinguished over the prior art in that the ultrasonic transducer is placed relatively close to the tissue sample being processed. The prior art uses a system in which the multipiece tissue sample is immersed in a liquid bath wherein the liquid bath is subjected to ultrasonic energy. The prior art method (low frequency ultrasound) results in much more tissue damage. The present invention can be used in a variety of histological, pathological, immunological and molecular techniques.

The present invention is directed to using high intensity, high frequency, nondestructive, wide-band ultrasound for tissue fixation and processing. The tissue must receive at least 10 W/cm$^2$ and fairly even distribution of the ultrasound. High intensities of the lower frequency ultrasound result in higher cavitation and are more harmful than higher frequencies.

The invention is directed to using a single high frequency or to using wide-band frequencies (0.1-50 MHz) high intensity ultrasound. The exact frequency and power to use to yield the best results depends on a variety of physical characteristics of the types of tissue being used.

The invention is directed to using ultrasound in conjunction with well known techniques to decrease the time required to perform the techniques, including immunological reactions, hybridizations, tissue fixation and processing, reactions on membranes as well as in tissues. The intensity of ultrasound used depends on the particular procedure and will be in the range of about 0.001-20 W/cm$^2$ Another aspect of the invention is that the complete process can be controlled and monitored by a feedback sensor-central processor unit (CPU)-ultrasound generation system. All of the steps of fixation and processing can be controlled by the CPU-ultrasound generation system. Use of a feedback sensor allows for optimization of the processes.

One aspect of the invention is the placement of an ultrasound transducer within 2 inches, preferably within 1 inch of the object being subjected to the radiation. Multiple transducers may be used to direct ultrasound to a single object.

The ultrasound being utilized can be either a continual lower intensity treatment or can be pulses of higher intensity of lower frequency.

DETAILED DESCRIPTION OF THE INVENTION

The rates of biological processes such as reaction rates of staining, hybridization, immunostaining, etc., as ell as processes such as fixing and imbedding tissue samples in paraffin can be increased by exposing the sample or tissue to ultrasound during the process. But as noted above, this unfortunately very often could be harmful to the biological sample. It has unexpectedly and fortuitously been discovered that the frequencies and power ranges disclosed herein exhibit superior results and substantially no or less tissue damage than the prior art methods. Low frequency ultrasound is harmful to tissues because it can cause cavitation. High frequency ultrasound is much less harmful. Unfortunately high frequency ultrasound is more easily absorbed by tissue. Nonetheless this can be overcome by using higher intensities of ultrasound in conjunction with the higher frequencies. Combining the proper frequency and intensity of ultrasonic treatment results in enhanced rates of reaction with no or minimal damage to the biological sample. The specific parameters depend upon the biological sample and the specific process being performed.

Over the past 50 years tissue fixation and processing has changed very little. Although MW irradiation has been applied in histology for tissue fixation to accelerate techniques such as histochemical staining, IHC, and antigen retrieval over the past 10-30 years, standardization of MW techniques and accurate monitoring of the procedures are still lacking (Login, 1998). Current methods of fixation and tissue processing are still like "batch or bulk cooking". Even the newly developed ultra-rapid MW/variable pressure tissue processor (Visinoni et al., 1998) uses the "batch or bulk method". Fixing and processing of needle and endoscopic biopsies from liver and stomach (small pieces of tissue) as Quell as large pieces of tissue from uterus and lung have been performed in the same bulk cooker. Large tissue is under fixed and small tissue is over fixed resulting in uneven fixation and processing. This type of variation makes it very difficult to perform IHC, ISH, PCR and other assays. In our preliminary studies, the prototype ultrasound apparatus was designed very roughly. The frequency and intensity chosen in this study were also not perfectly optimized. Nonetheless, the studies have generated excellent morphology with good protein and RNA preservation. No doubt, standardization of ultrasound-mediated high-speed tissue fixation and processing techniques and accurate monitoring of the procedures should further decrease the time and improve the quality of results. This can be accomplished by controlling all steps of fixing and processing by means of a sensor-central processing unit (CPU)-ultrasound generator feedback system. Ultrasound sensors monitor and determine how much ultrasound is absorbed by solution and/or tissue. The size, type, density, water content, and other information of the tissue are measured by ultrasound sensors before fixing and processing. The sensors send all digitized data information to the CPU. The CPU analyses the digitized data and sends parameters to the ultrasound generator that in response emits the proper frequency and intensity of ultrasound for a measured tissue. During processing, the changes of tissue size, thickness, density, water content, solvent content, paraffin content and other information are accurately monitored and detected by sensors which continuously send changed digitized data information to the CPU and rejustify the ultrasound generation system. This is similar to an acoustic force microscope or ultrasound scanner that sees inside tissue where a digital signal is converted to an image showing differences in density. During fixation the density of the sample changes. The CPU can be programmed to change the solution when the sample reaches a specified density. Under this kind of emission-monitoring system, 1) the fixed and processed tissue is always in perfect or optimal condition; 2) the processed tissue avoids damage caused by too aggressive ultrasound emission and over-fixation caused by the tissue remaining too long in fixative: 3) individual tissue processing can be standardized and tissue fixation optimized to avoid "bulk cooking", and 4) different sizes of DNA or RNA probes will react with DNA or RNA targets or different affinities of antibodies will react with antigens under optimal match conditions.

The preferred range of ultrasound frequency is in the range of 100 KHz to 50 MHz. A frequency in the range of 0.1 to 1 MHz can be used but only at a low power range of 0.1-25 W/cm$^2$ or else cavitation will occur. Use of 1 MHz to 10 MHz is less destructive than the lower frequencies and allows the use of higher power (20-100 W/cm$^2$) which helps chemicals penetrate into the tissues. Higher frequencies such as 10-50 MHz increase the rate of reaction even further but tend to generate heat and at these higher frequencies it again is necessary to lower the power to about 5-50 W/cm$^2$, here for the purpose of limiting the heat produced.

The process of combining ultrasonic treatment with well known biological methods is further enhanced by placing the ultrasound treatment under computer control in which part of the process or the complete process is controlled by inputting various parameters concerning the technique being performed, data concerning the tissue composition (e.g., bone, fat, etc.), size, etc., and be use of a sensor to monitor the ultrasound.

The mechanism of the ultrasound fixation and processing methods has not been established. However, the basic principles of ultrasound may explain the process. Ultrasound has long been employed in such diverse medical fields as physical therapy, kidney and gall stone ablation, and medical diagnostics. Abundant information exists about both its biological effects and potential toxicity (Miller, 1991). Many phenomena, including cavitation, thermal effects, generation of convective velocities, chemical effects, biological effects, and mechanical effects, have been considered to play an important role in the ultrasound-mediated enhancement of fixation and processing (Miller et al., 1996). We have utilized the well-known fact that intense ultrasonic waves traveling through fixative, solvent and tissue generate cavitations that enlarge and implode creating tremendous power. These extreme conditions provide an unusual chemical reaction which man result in acceleration of hydration of methylene glycol to formaldehyde. acceleration of its binding to various amino acids, and acceleration of fixing, dehydrating, clearing and impregnating tissue in an extremely short time. Based on the same principles of ultrasound, we have applied ultrasound to immunology and molecular biology for accelerating reactions such as immunologic reaction, hybridization washing and deparaffinizing.

Figure 1:
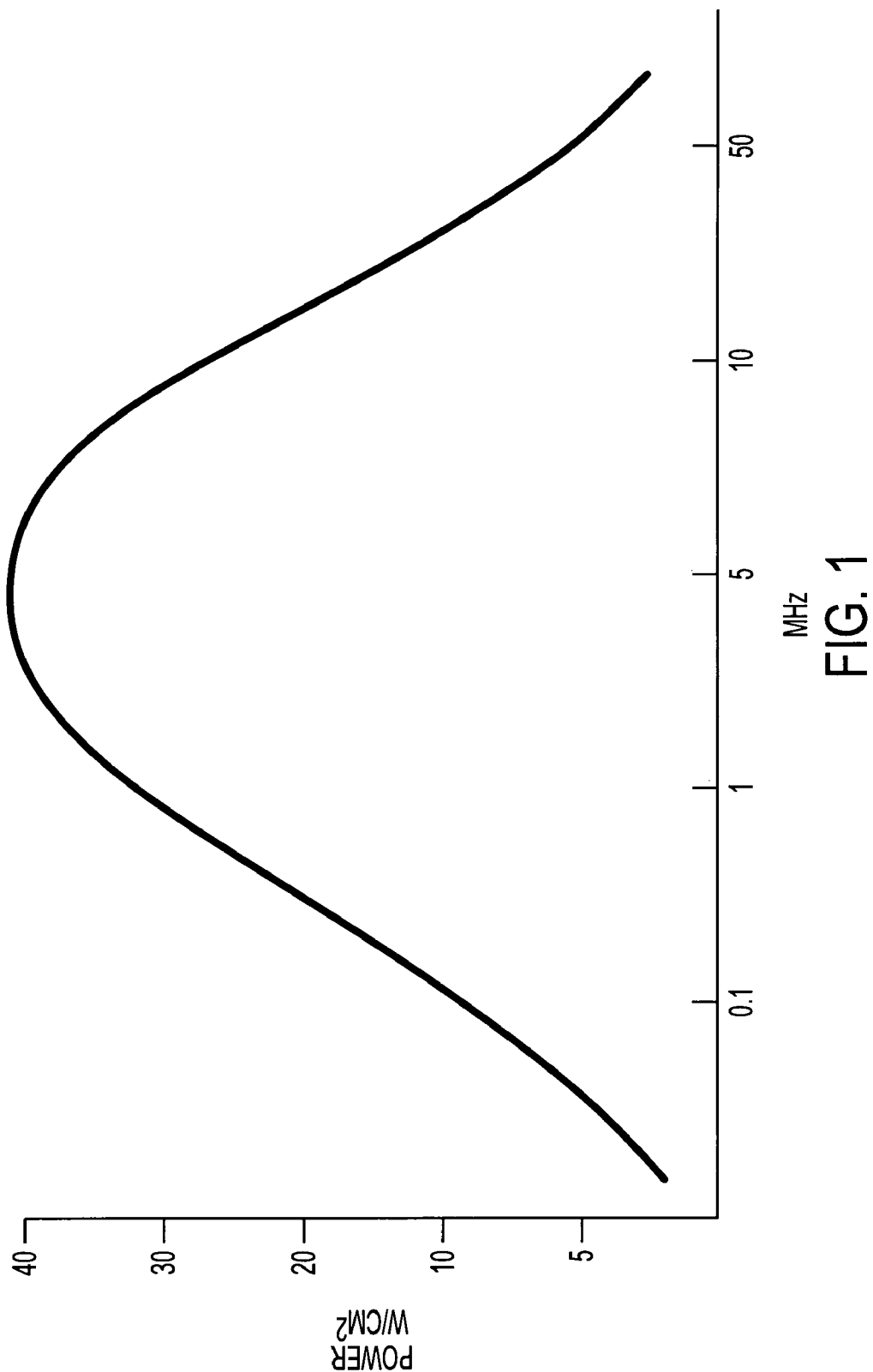
FIG. 1 is a diagram showing frequency generated vs. power of ultrasound produced by a transducer. In this diagram the power is strongest at a frequency around 5 MHz. At higher and lower frequencies the power decreases. The exact values obtained depend upon the transducer which is used, the characteristics of tissue or sample being treated, and the solution or solvent which is used.

One aspect of the invention is the use of transducers with multiple heads. It has been found that use of a broad band of frequencies simultaneously during the processes can improve the process. A single head is less efficient at producing a wide range of desired frequencies. To overcome this shortcoming each transducer can be fitted with multiple heads with each head on a transducer covering a different range of frequencies. FIG. 1 illustrates broadband, high-frequency, high-intensity ultrasound generated by a single transducer. Power is greatest in the mid-range of frequencies with low power at the lose and high frequencies. Low frequency ultrasound is destructive to tissue, but this destructiveness decreases as the frequency is increased. Conversely, low frequency ultrasound produces only a small amount of heat, but heat generation increases as frequency increases. The use of broadband (or wideband) ultrasound is useful because tissue heterogeneity and different solvents result in different requirements for the specific tissue and process being used. Consequently a system with the ability to generate a broad band is preferred although not required. Multiple transducers can also be used to achieve broadband ultrasound emission and to generate a desired power level at a desired frequency.

Another aspect of the invention is irradiating the sample from multiple directions. This can be accomplished in a variety of ways. A single transducer can be moved relative to the sample either by rotating the sample or by revolving the transducer around the sample. Alternatively, several transducers can be used simultaneously with the transducers set out in, e.g., a circular pattern around the sample. If desired, multiple transducers can be set out in a 3-dimensional pattern about the sample rather than the 2-dimensional pattern of a circle or the 1-dimensional pattern of a single transducer.

It is preferable to use a system which results in an even distribution of ultrasound energy throughout the reaction chamber. Use of a single, small transducer can result in uneven distribution of ultrasound and the positioning of the tissue within the reaction chamber could have a large effect upon the results, especially if using a system without any sort of feedback to control the ultrasound generator. Such a system makes it easy to overfix or underfix a sample. An even distribution of ultrasound energy throughout the reaction chamber is preferred. This may be achieved by use of multiple transducers set out around the reaction chamber, by use of a single, well designed transducer which will put out an even signal across the reaction chamber, and/or by use of a well designed reaction chamber.

A further aspect of the invention is the use of sensors to determine the progress of the treatment such that it can be determined when to stop the treatment. Preferably this will be computer controlled by connecting the sensors and the transducers to a central processing unit. As a tissue sample is fixed, the intensity of ultrasound reflecting from or passing through the tissue changes. This change is detected by the sensors and fed into the central processing unit. When the signal reaches a preset level the central processing unit will shut off the transducer producing the ultrasound reflecting from or passing through the tissue to that sensor. In this manner there is assurance that the tissue is neither undertreated nor overtreated with ultrasound. The exact settings will depend on factors such as the type and thickness of sample being treated and the frequency and power of ultrasound being used. Such settings can be determined by one of skill in the art with some initial trial and error testings. Once determined for a type of tissue and thickness of that tissue the value can be used for all future samples of that type and thickness and the frequency and power settings used with no need of testing further. This holds true not only for tissue fixation but also for any other procedure for which ultrasound is being used.

The idea of measuring the intensity of reflected ultrasound or of ultrasound passing through the sample is similar to that of measuring ultrasound to assay for cracks in metals or ceramics. This is well known in the prior art of those fields although those fields are quite different from the fields of pathology and molecular biology.

Figure 2:
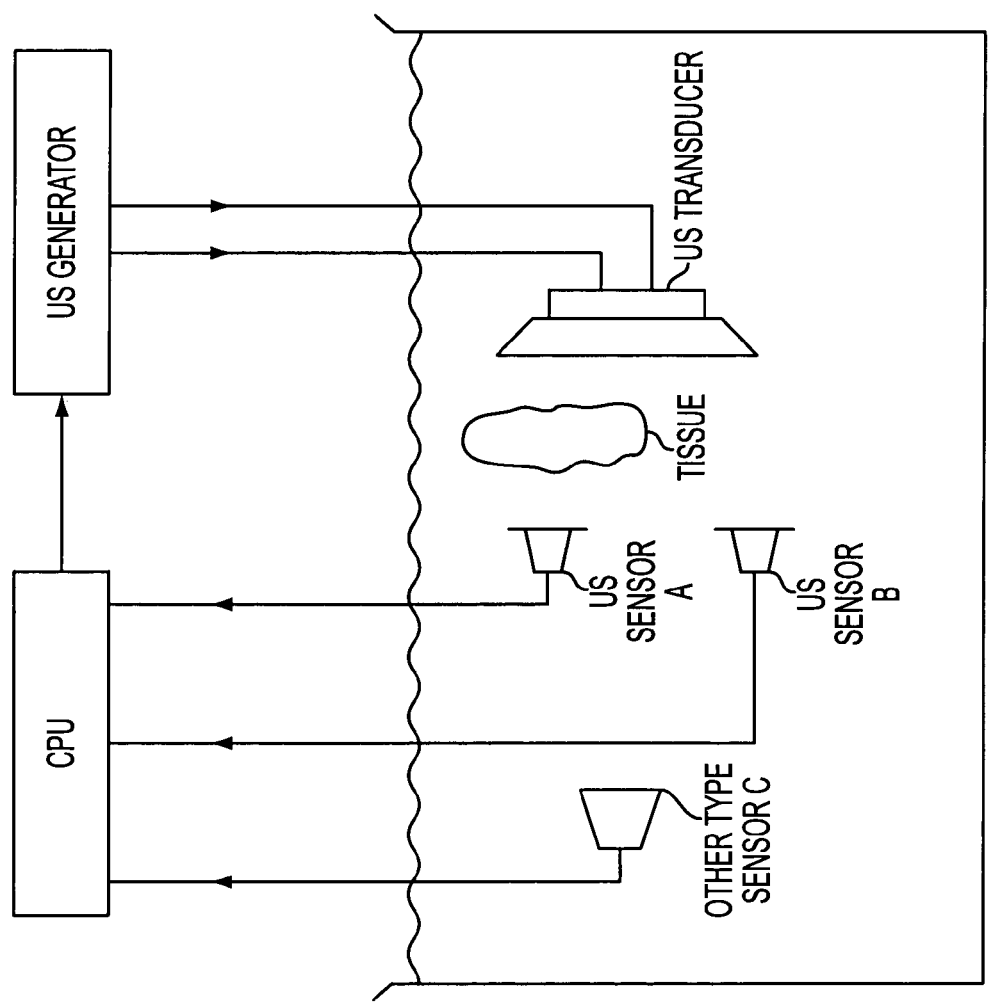
FIG. 2 is a schematic diagram showing a tissue in a buffer being treated with ultrasound. An ultrasound generator controls a transducer which produces the ultrasound waves. Three sensors. A, B and C, are shown. A central processing unit (CPU) controls the ultrasound generator as well as records data from the sensors.

One setup for treating tissue with ultrasound is shown in FIG. 2. An ultrasound generator causes a transducer to emit ultrasound waves of a desired intensity and frequency, with a range of intensities and frequencies being used if desired. Tissue is placed in solution together with the transducer and is exposed to the ultrasound waves produced by the transducer. Although it is quite feasible to simply use a transducer and a piece of tissue and to expose the tissue to ultrasound at a desired frequency and intensity for a specific length of time, the method can be improved by including one or more sensors to follow the reaction, e.g., fixation, impregnation with paraffin, etc. Sensor A is used to monitor the intensity of the ultrasound which passes through the tissue. The intensity will change over time as the reaction, e.g., impregnation with paraffin, proceeds. The signal from sensor A can be fed into a central processing unit (CPU) which in turn regulates the ultrasound generator and can be programmed to adjust the intensity and/or frequency of the ultrasound being produced by the transducer. It can be desirable to change the intensity and/or frequency as the process proceeds, e.g., as the tissue takes up more paraffin or as it becomes more dehydrated, depending on the process being performed. A second sensor (sensor B) can also be used if desired. Sensor B measures the ultrasound intensity in the solvent or solution in which the tissue is placed. It measures this in a region such that it measures the intensity of ultrasound which has not passed through the tissue. This effectively serves as a baseline measurement which will depend not only on the signal produced by the transducer but also depends upon the specific solvent or solution. Consequently it can be used to account for the use of different solvents or solutions. As with sensor A, the signal received by sensor B can be fed into a CPU which controls the ultrasound generator. The use of a third sensor can also be accommodated. For example, sensor C, which may be a temperature sensor, such as an infrared temperature sensor, can be used to monitor a physical parameter of the tissue during the processing of the tissue, e.g., sensor C can be used to measure the temperature of the tissue. Again, this information can be fed back to the CPU and be used to regulate the ultrasound generator throughout the time course of the process. For example, if the temperature of the tissue was getting too high a signal could be sent to decrease the intensity of the signal, to alter the pulsing of the signal, or to turn off the signal for a time until the temperature decreased to a specified temperature. Further sensors can be added to the system as desired. Furthermore, one can use any one sensor without the others, e.g., sensor C as described above to measure a physical parameter could be used alone in the absence of sensors A and B. Also, as noted above, it is unnecessary to use any sensors although it is preferable to do so because the feedback system enabled by the sensors helps prevent overprocessing or underprocessing of the tissue.

Figure 3A:
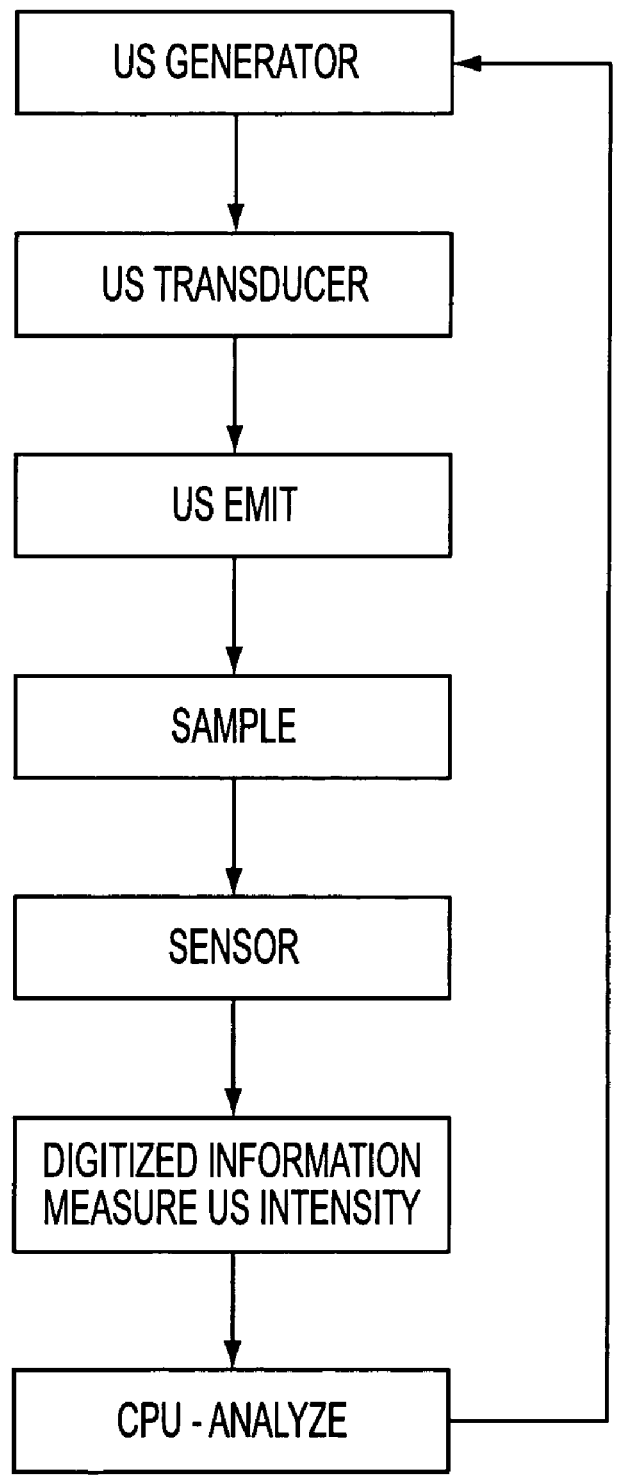
FIG. 3A illustrates a monitor feedback system. The sensor measures the ultrasound intensity which passes through the sample and feeds this to a CPU which feeds back to regulate the ultrasound generator.
Figure 3B:
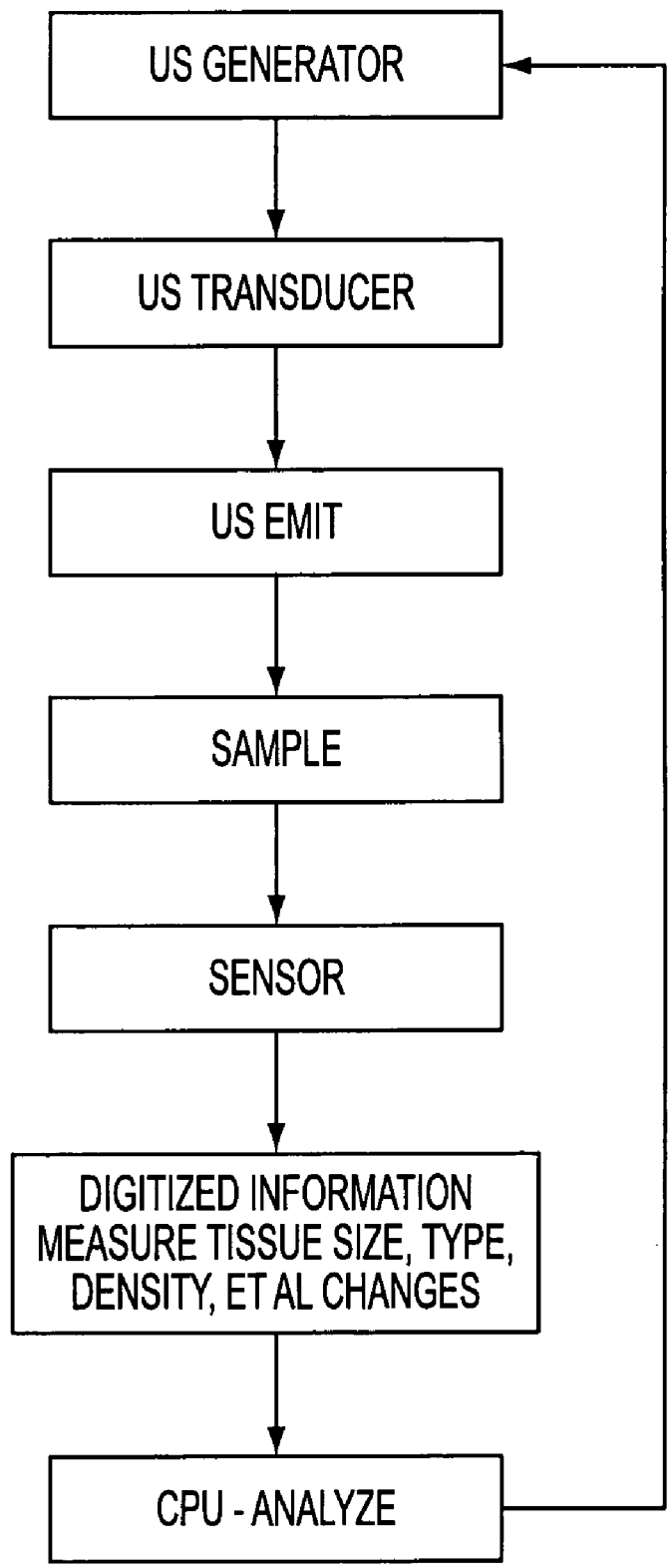
FIG. 3B illustrates a monitor feedback system in which sensors monitor and/or measure parameters, e.g., size, type, density, etc., of a sample and feed data to a central processing a unit which feeds back to an ultrasound generator controlling a transducer producing ultrasound waxes which irradiate a sample.

Some examples of the above processes are shown as flow diagrams. FIG. 3A shows a flow diagram for a system utilizing a single sensor. An ultrasound generator controls an ultrasound transducer which emits ultrasound of a desired frequency and power. The ultrasound passes through a tissue and is detected by a sensor. The sensor sends a signal to a CPU which analyzes the signal and, if desired, digitizes the signal, and in accord with a program controls the output of the ultrasound generator. FIG. 3B is a flow diagram of a system similar to that shown in FIG. 3A except that the sensor, which may be a temperature sensor, such as an infrared temperature sensor, measures a physical parameter of the tissue sample, e.g., size, type, density, temperature, etc.

Figure 4:
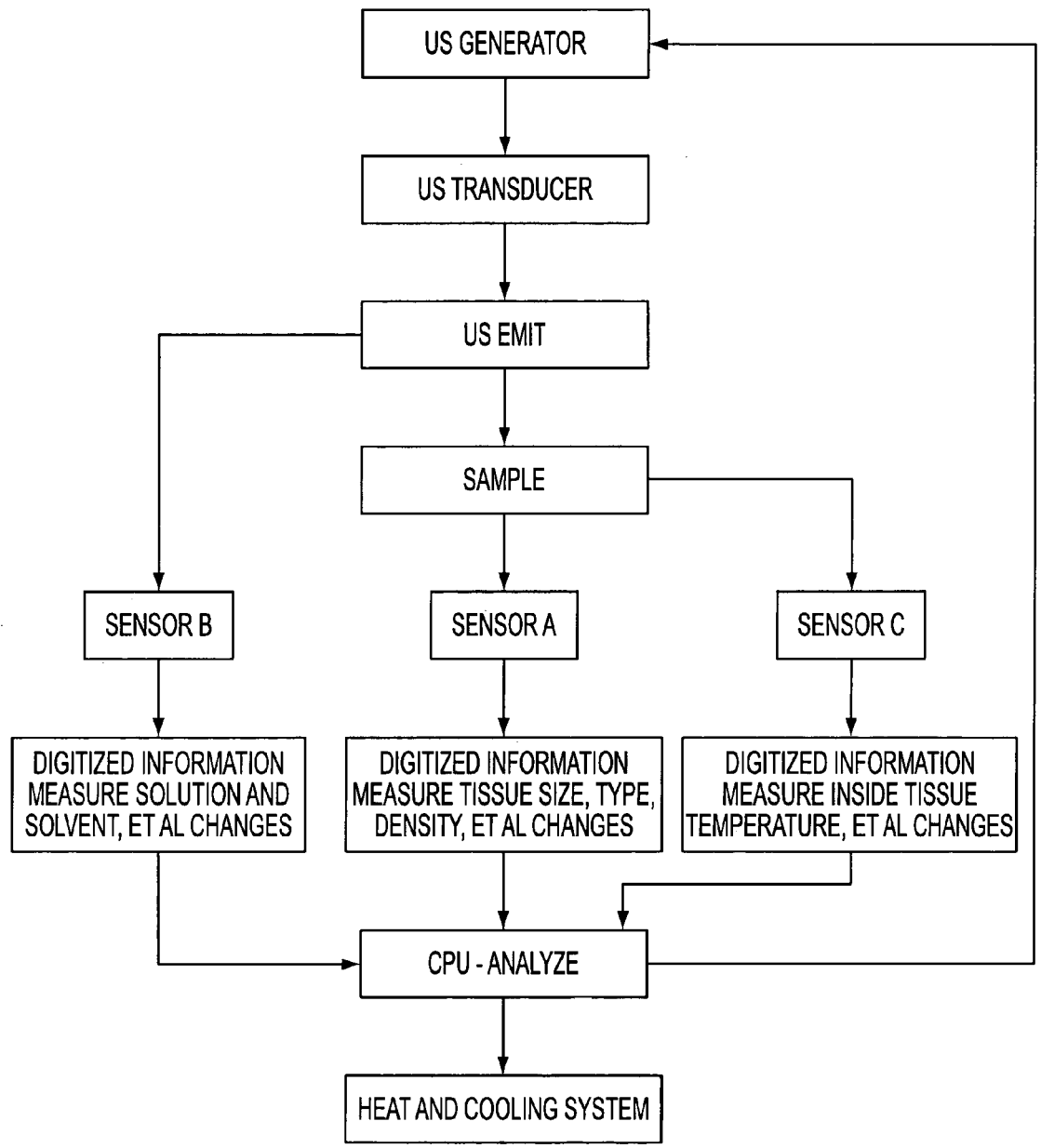
FIG. 4 illustrates a second type of monitor feedback system. This system includes 3 sensors. Sensor B monitors the ultrasound emission, sensor A monitors a property of the sample, and sensor C monitors a property of the sample. Information from the sensors is fed to a CPU which feeds back to control the ultrasound generator as well as a heating and cooling system.

FIG. 4 shows a flow diagram of a system using three sensors. In this system an ultrasound generator causes a transducer to produce ultrasound, some of which passes through a tissue sample and some of which passes only through solution, e.g., a fixative or a solvent. Sensor A measures the ultrasound signal which passes through the tissue and feeds this signal to a CPU for analysis. Sensor B measures the ultrasound signal which passes through the solvent/solution only and feeds this signal to a CPU. Sensor C does not measure an ultrasound signal, rather it is used to measure a physical parameter of the tissue itself. Sensor C also feeds a signal to a CPU for analysis. The CPU (or CPUs if more than one is used) analyze the data, digitize it and feed back to control the output of the ultrasound generator in accordance with a program. For example, the system can be programmed to shut off once the tissue reaches a specified density or a specified size or it may be shut off when the signal measured b sensor B in this example reaches a specified intensity. Alternatively the system can be programmed to adjust the intensity and/or frequency of the sound waves produced by the transducer or to adjust whether to give off a continuous signal or a pulsed signal as well as adjusting the rate of pulsing if a pulsed signal is used. For example, it is useful to alter the frequency during fixation of tissue, with a high frequency being used early and a low frequency being used later as the tissue becomes fixed.

Figure 5A:
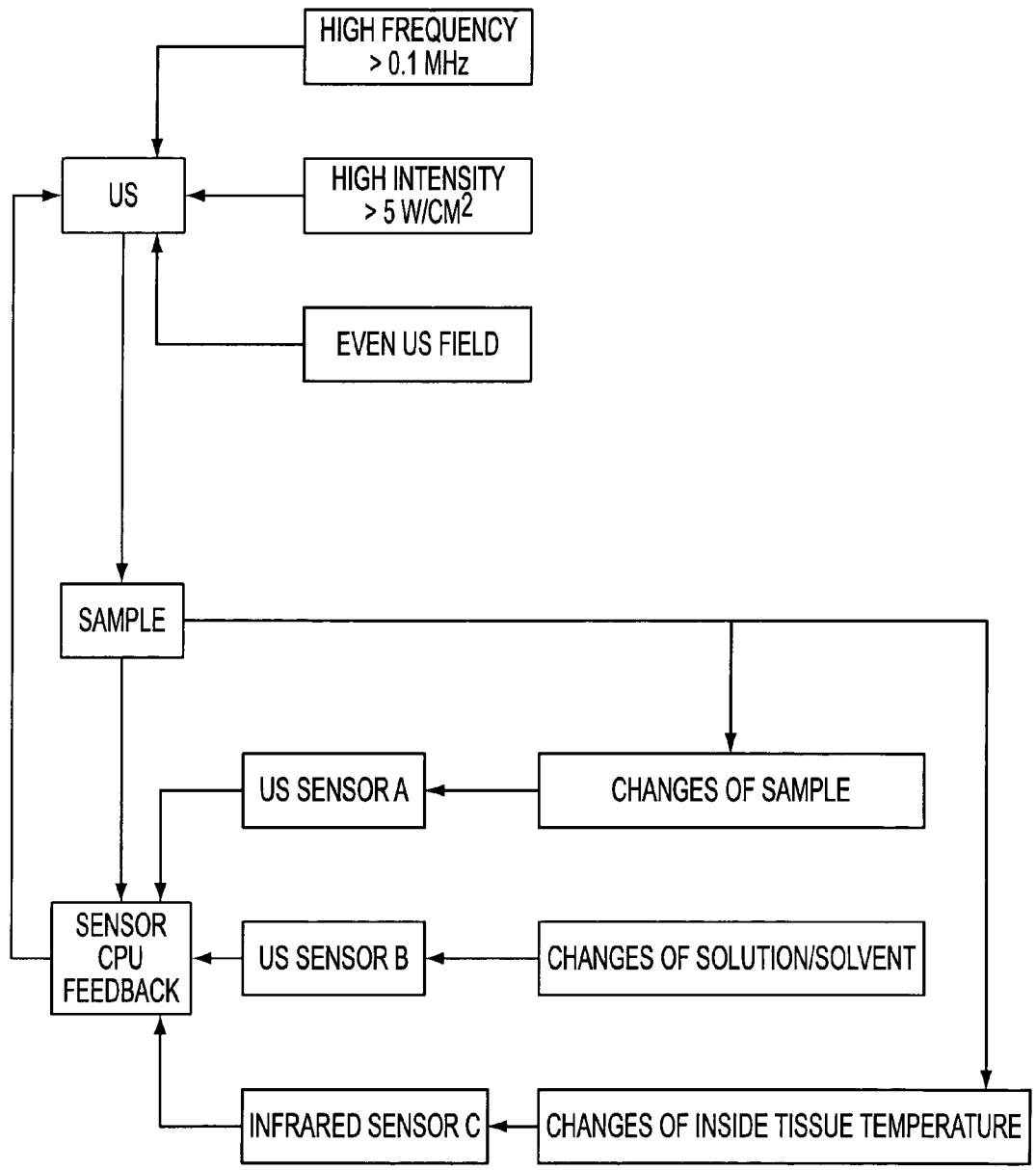
FIG. 5A is a schematic of a setup for performing fixation and processing of a tissue sample using ultrasound as part of the process. An ultrasound generator (US) produces ultrasound which irradiates a sample. One sensor monitors the ultrasound, and other sensors monitor the sample as well as the solution/solvent. This data is processed and used by the CPU to automate changes in sample and/or solution or solvent. Data from the temperature sensor can be used to regulate the ultrasound output so that the temperature does not get too high.
Figure 5B:
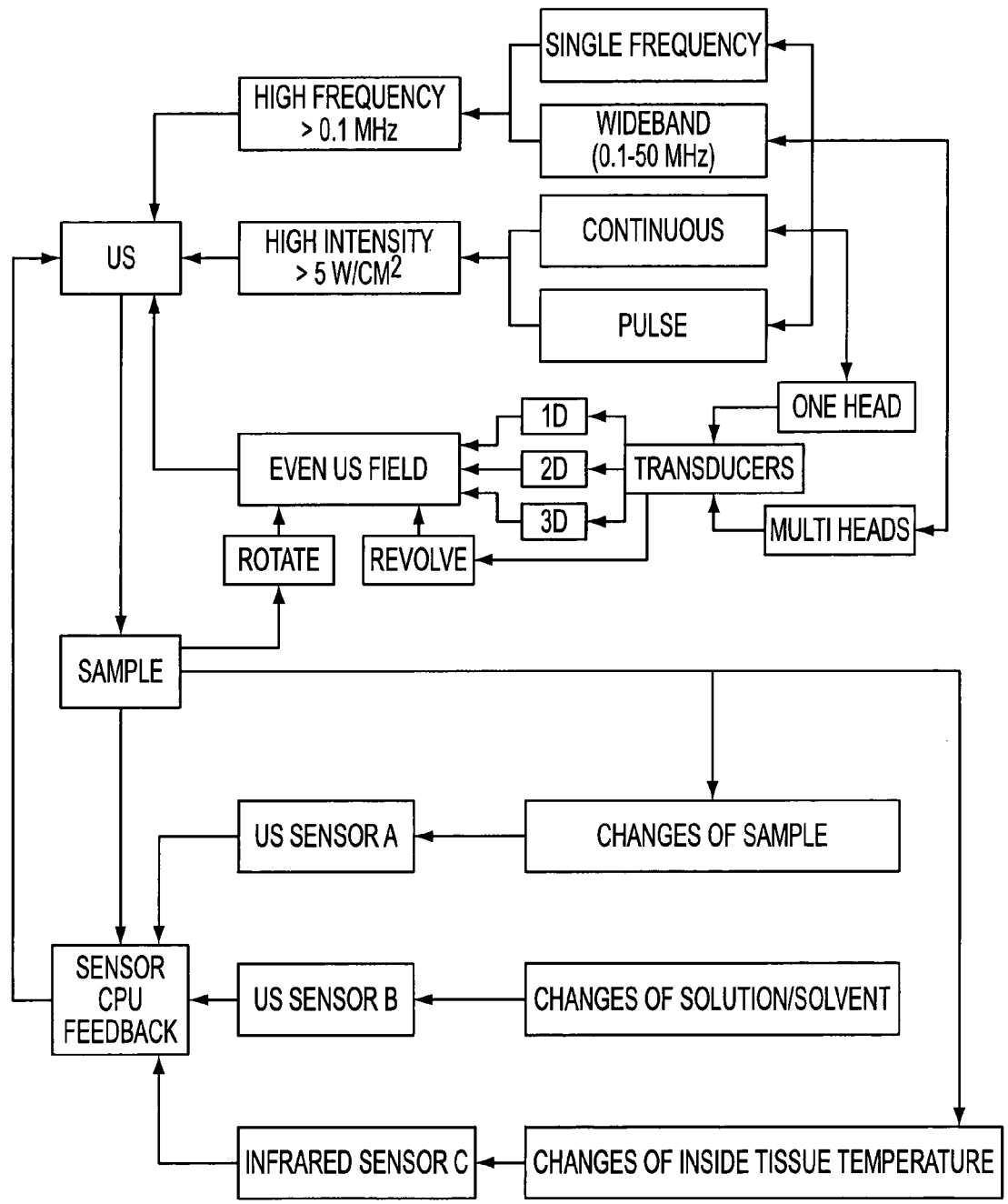
FIG. 5B is a schematic of one possible setup for performing fixation and processing of a tissue sample while using ultrasound as part of the process. It is similar to the setup of FIG. 5A but includes more aspects. The ultrasound generator puts out high frequency, high intensity waves which can be of a single frequency or a wideband frequency and can be continuous or pulsed. The transducer or transducers can have one head or multiple heads. The sample can be rotated or the transducers can revolve around the sample to aid in producing an even ultrasound field. This can be performed in one, two or three dimensions (1D, 2D and 3D).

A more general ultrasound system setup is illustrated in FIG. 5A. An ultrasound generator produces ultrasound which irradiates a sample. Sensors are present to measure the incident ultrasound intensity and can also measure ultrasound intensity which passes through the sample, size of the sample, temperature of the sample, etc. Data from the sensors feeds into a central processing unit which can control the ultrasound generator as well as control movement of samples into and out of a reaction chamber, change solution or solvent within a reaction chamber etc. Preferably when this is used for fixation and processing of a tissue sample a high frequency >0.1 MHz and high intensity >5 $W/cm^2$ is used. An even field of ultrasound radiation is also preferred. FIG. 5B represents further options including use of either a single frequency or a wideband of frequencies of ultrasound radiation. The radiation can be continuous or given in pulses. Transducers can have one head or multiple heads. To produce a more even field of radiation on the tissue sample, the sample can be rotated and/or the ultrasound transducers can be revolved around the sample.

Figure 6A:
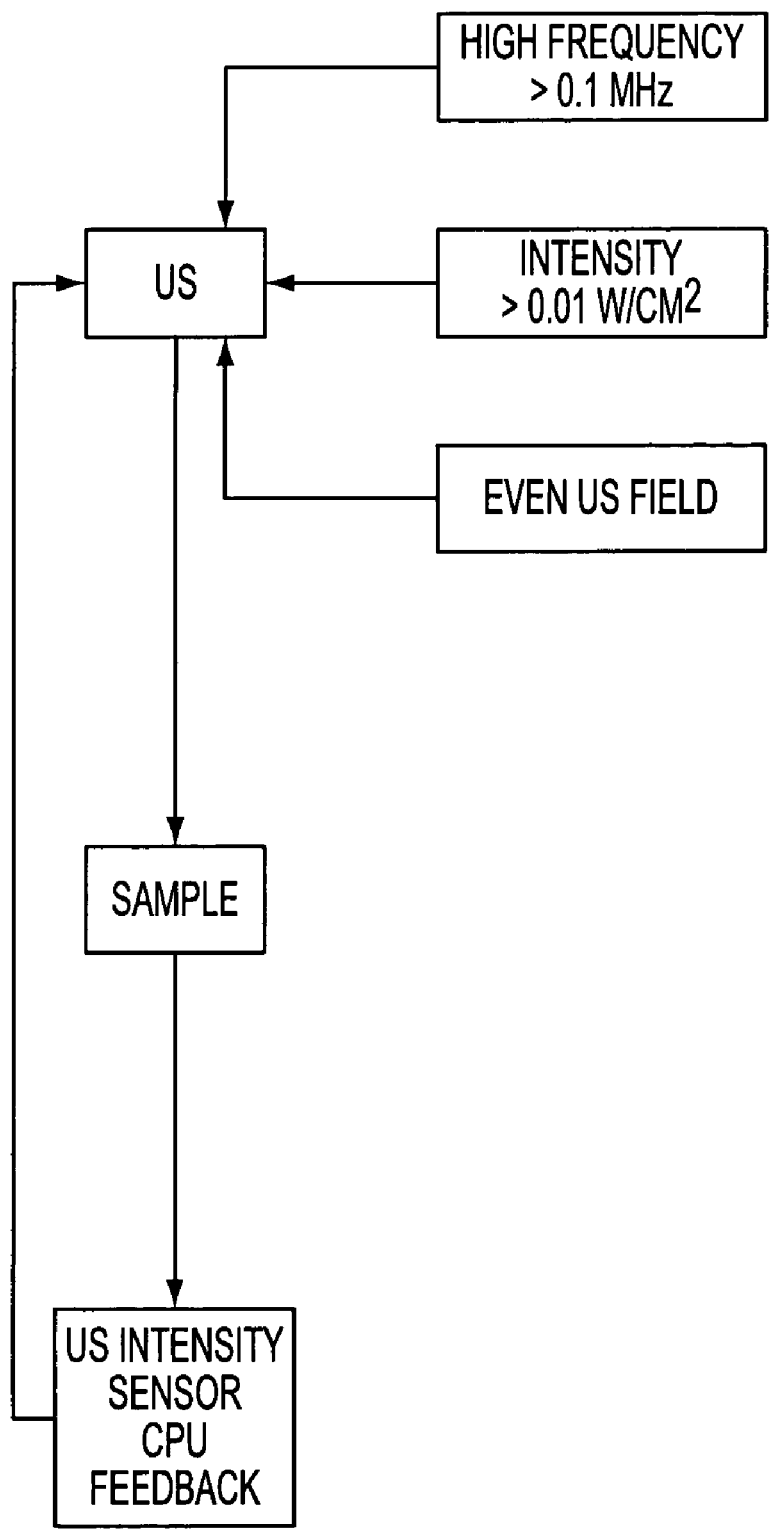
FIG. 6A is a schematic of one possible system for performing and monitoring a biological reaction using ultrasound. It is similar to FIG. 5A but only one sensor is shown which is used to monitor the ultrasound intensity. Also, the intensity of the ultrasound being used is lower in this system.
Figure 6B:
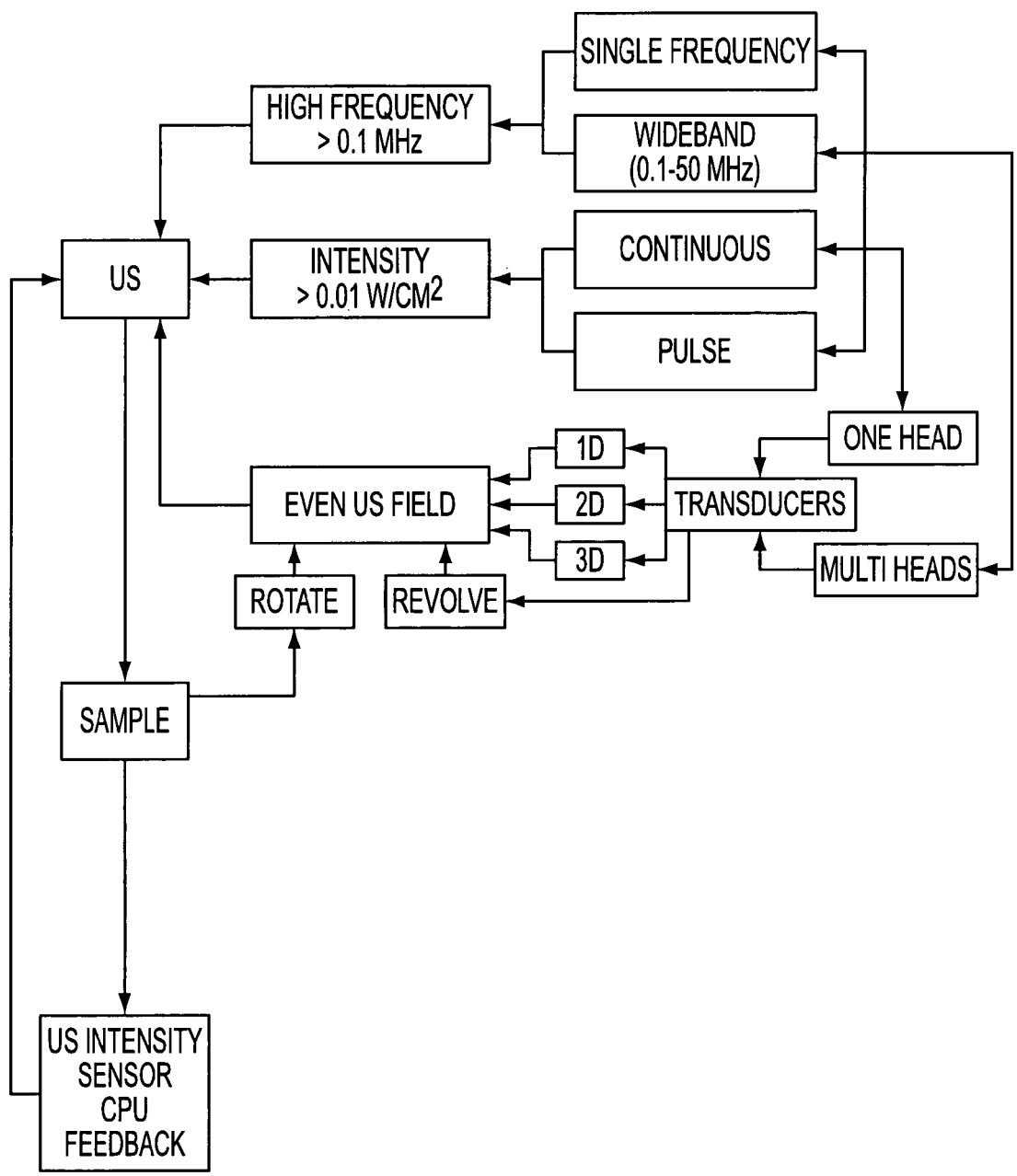
FIG. 6B is a schematic of one possible system for performing and monitoring a biological reaction using ultrasound. It is similar to FIG. 9 but only one sensor is shown which is used to monitor the ultrasound intensity which is lower in this system.

FIGS. 6A and 6B outline setups for performing biological reactions. These are similar to what is shown in FIGS. 5A and 5B for fixation and processing of tissue samples. For biological reactions the intensity of the ultrasound radiation still be much lower and there is less need to monitor physical parameters of the sample, although such can be done if desired.

The experiments described herein use high frequency and high intensity ultrasound for tissue fixation. The ultrasonic apparatus used in the present study consists of an ultrasonic generator and a 1.6-1.7 MHz ceramic transducer with an adjustable output intensity range from 1 to 22 W/cm$^2$. The safety range of this high frequency ultrasound irradiation has been tested with a variety of different tissue sections in several different solutions including saline, 10% neutral buffered formalin (NBF), different concentrations of alcohol, xylene and 60° C. paraffin using a variety of different ranges of ultrasound intensity. The structure of a 5µ tissue section mounted on a microscope glass slide continuously irradiated with 1.6-1.7 MHz ultrasound at 20 W/cm$^2$ intensity (actual intensity received by the tissue) in a variety of buffers or solvents for 10-20 minutes did not show any difference as compared to an untreated neighboring serial section when viewed by light microscopy. However, neighboring serial sections were destroyed when irradiated in a 40 kHz ultrasound cleaning water bath for 10 seconds in a variety of buffers or solvents (Yasuda et al., 1992). These results indicate that high frequency and high intensity ultrasound irradiation is very safe for thin tissue sections.

Fresh surgical specimens were cut into 3-4 mm slices. One slice of tissue sample was step-by-step placed in NBF, steps of alcohol, xylene, and 60° C. paraffin and immediately irradiated by 1.6~1.7 MHz ultrasound at 20±3 W/cm$^2$ intensity (actual intensity received by the tissue). Other slices of tissue samples were subjected to a standard fixation (overnight) and processing (overnight) as controls. Consecutive 4-5µ sections were cut from an ultrasound treated block and a control block. The sections from both blocks allow parallel comparison of morphology (hematoxylin and eosin staining (H&E)), protein (immunohistochemistry (IHC)) and RNA (mRNA in situ hybridization. (mRNA ISH)) preservation. The size of mRNA templates preserved by the ultrasound and routine methods was further observed with RT-PCR.

The sections from ultrasound treated tissue were excellent in histologic appearance as compared with their routine fixation and processing counterparts. The color balance in the H&E ultrasound section consistently demonstrated slightly more eosinophilia on the cytoplasm and more intense nucleus staining than the routine method (FIGS. 10A-B). All ultrasound irradiated tissue blocks sectioned as well as control tissue blocks and no difference was detected in the sectioning and staining process. No evidence of cavitation tissue injury was noted in the ultrasound treated specimens under the conditions employed in this study. Ultrasound treated tissue sections following protease or MW antigen retrieval pretreatment showed no disintegration or deterioration. This indicates that tissue is fixed by formalin rather than by alcohol (dehydration only 10-15 minutes) according to Azumi's explanation (Azumi et al., 1990).

The distribution of IHC for CD45, CD20, CD3, CD5, Bcl-2, cytokeratin, kappa and lambda from routine or ultrasound treated tissue sections is similar in this study. Several of the factors involved in the process of fixation were found to affect immunoreactivity of the antibodies used in this study. These include the duration and the speed of fixation and processing, and the duration and the concentration of primary and secondary (2°) antibody incubation. A short incubation with primary/2° antibodies/ABC (10 minutes/5 minutes/5 minutes) gave poor staining results compared to the overnight incubation. However, this method gave the best measurement to evaluate the condition of antigen preservation. The tissue from ultrasound irradiated fixation and processing significantly improved the immunoreactivity of the majority antibodies (CD3) in this study, and also dramatically reduced the incubation time. The requirement of concentration of primary antibodies (cytokeratin) for ultrasound treated tissue also was reduced more 20-fold compared to the routine treated tissue. Ultrasound high-speed fixed and processed tissues demonstrated the optimal fixation condition that was stained by CD5 even without MW antigen retrieval pretreatment (FIGS. 11A-B).

ISH is an excellent method for visualization and accurate detection of a specific gene (e.g., oncogene, tumor suppressor gene or viral gene) in individual, morphologically defined normal and neoplastic cells in both fresh and archival tumor specimens with light microscopy. mRNA ISH is one of the best methods to evaluate the condition of tissue mRNA preservation (Weiss and Chen, 1991; Harper et al., 1992). Since the poly d(T) probe presumably hybridizes to polyadenylated sequences of RNA, it would be expected that this probe would hybridize to the majority of mRNA species—only 10-30% of mRNA lack the polyadenylated tail. Ultrasound high-speed fixed and processed tissue dramatically improved the total polyadenylated mRNA preservation more than 20-fold in the periphery and more than 100-fold in the center of tissue as compared with the routine method (FIGS. 12A-B). As a check on the validity of the poly d(T) used to detect mRNA, we performed parallel studies to detect a specific mRNA, using the probes recognizing kappa immunoglobulin light chain mRNA. The even distribution of kappa mRNA protected was found in the tissue treated by the ultrasound method. However, in the tissue treated with the routine method, the periphery and center showed uneven distribution, i.e., there was good fixation of the tissue at the periphery and good preservation of mRNA at the periphery due to inactivation of RNAse in that region therefore showing good results, but the more interior regions of the tissue were not well fixed and mRNA was not well preserved and showed poor results.

The mRNA ISH is only to examine the quantity of mRNA preservation in the tissue section. For assessment of the quality of mRNA samples generated from routine or ultrasound fixed and processed tissues. RT-PCR was performed with two different sets of primer pairs to amplify β-actin mRNA which was then detected with ethidium bromide (Fend et al., 1999a: Ben-ezra et al., 1991: Foss et al., 1994: Krafft et al., 1997). With the two sets of primer pairs used in this study, the expected sizes of the cDNA amplification products were 156 bp and 548 bp. The routine method and the ultrasound treated FFPE tissue block (FFPE blocks there stored at room temperature for 5 to 6 weeks until used) samples yielded extractable RNA using the TRIzol LS technique (Krafft et al., 1997). RNA yields were similar. Fixation and processing by the routine method required 32 hours and yielded 0.17 µg/µL of RNA with an $A_{260}/A_{280}$ of 1.536. Using the ultrasound method, fixation and processing required on the order of 1 hour and yielded 0.19 µg/µL of RNA as with an $A_{260}/A_{280}$ of 1.655.

RT-PCR of mRNA from both the routine method and the ultrasound treated tissue blocks produced a PCR 156 bp product, with the samples treated with ultrasound producing a comparatively stronger band. Shorter products were amplified more efficiently than longer products, but β-actin mRNA fragments of 548 bp were successfully amplified from the ultrasound treated tissue block (FIG. 13). No 548 bp signals there observed after amplification from routine FFPE tissue block and negative RT controls (no addition of reverse transcriptase). It has been reported that it is difficult to amplify any mRNA larger than 200 bp in FFPE tissues (Fend et al., 1999a; Ben-ezra et al., 1991; Foss et al., 1994, Krafft et al., 1997).

The results of this study demonstrate that the ultrasound-fixing and -processing method provides excellent morphologic detail as shell as excellent preservation of a variety of protein antigen and mRNA within one hour. It shows that ultrasound energy can have an important role in rapidly fixing and processing biologic samples for quick diagnosis, immunology and molecular biology study. The ultrasound method provides certain advantages over the routine method for performing IHC for some of the antigens evaluated in this study. For example, tissues fixed and processed by the ultrasound method 1) did not require MW antigen retrieval for the detection of CD5. 2) allowed the IHC to be completed within 20 minutes, and 3) allowed use of a very low concentration of antibody (high affinity antigen-antibody reaction). Furthermore, RNA is very unstable in tissue once removed from the body. High levels of endogenous RNase must be inactivated before RNA and mRNA degradation. Demonstration of RNA preservation in this study shorts that the RNase enzymatic activity was sufficiently inactivated within 10 to 15 minutes by ultrasound fixation and processing (dehydration in ethanol, clearing in xylene and infiltration with paraffin for 15 minutes each) in 45 minutes. The results show that the ultrasound method provides a high quantity of mRNA preservation in the periphery and in the center of tissue blocks used for ISH, and a high quality of mRNA preservation by RT-PCR. Several possibilities may be responsible for the differences observed in the quantitative mRNA ISH and qualitative yields of RT-PCR products between these two methods. First, routine fixation requires a long time (12-18 hours), whereas ultrasound fixation occurs in less than 10-15 minutes. The longer exposure of the fresh tissues to the fixative before embedding in paraffin may result in RNA degradation from endogenous RNases, resulting in a smaller size of amplifiable RNA. Second, although inactivated RNases are reversible within 24 hours, the degree of RNase inactivation, cross-linking reaction, and the rate of fixative penetration into the tissue may be time dependent in the routine method. Third, the presence of residual fixative in the extracted cells man affect the efficiency of the RT or PCR reaction, resulting in a reduced amount of amplicon produced with samples prepared by the routine method. All results suggest that the rapid ultrasound method is a valuable technique to permit or archive optimal preservation of antigen proteins, as well as being useful for light quantity and quality RNA preservation.

The results of the instant study demonstrate that the ultrasound-fixation method provides excellent morphologic detail as well as excellent preservation of a variety of protein antigens and mRNA in a matter of minutes. It shows that ultrasound energy has an important role in rapidly fixing biological samples for quick diagnosis and for immunological and molecular biological studies. The optimal fixation is extremely important for preservation of natural structure of antigen proteins and inactivation of enzymatic activity. The protein enzymatic activity must be inactivated very quickly and completely after biopsy. High levels of endogenous RNase must be inactivated before RNA and mRNA degradation can occur.

Formaldehyde, when dissolved in eater, quickly changes to methylene glycol and its polymers Kith less than 0.1% of the formaldehyde remaining in solution although the methylene glycol penetrates tissue very rapidly. Chemical cross-linking with tissue is a relatively slow processing "clock reaction" that depends on the release of free formaldehyde by gradual hydration of methylene glycol to produce formaldehyde. The available free formaldehyde binds to various amino acids (Fox et al., 1985). The reaction with tissue is largely reversible over the first 24 hours, and the fixed surface tissue acts as a barrier to subsequent inward diffusion of fixatives. Ultrasound-energy overcomes these disadvantages and achieves the optimal fixation. The range of optimal fixation (retaining the natural structure of antigen proteins without enzymatic activity) is relatively narrow, but is achieved with ultrasound fixation.

Ultrasound fixation provided certain advantages over routine formalin fixation for the IHC of some of the antigens evaluated in this stud. For example, tissues fixed by the ultrasound method did not require MW antigen retrieval for good detection of CD5 whereas the corresponding formalin-fixed specimens did require MW treatment. However, using pepsin or MW antigen retrieval pretreatment provided the best results for IHC (Tables 3-4). Furthermore, ultrasound fixed specimens were superior to routine formalin fixed tissues for the IHC performed for short times (high affinity antigen-antibody reaction). These results indicate that the ultrasound fixation method of the instant disclosure is a valuable technique for achieving optimal preservation of antigen proteins which are altered when the routine fixation method is used. The results also indicate that the natural structures of antigen epitopes fixed by ultrasound retain their high affinity to react with antibody.

We have treated tissue samples with both IHC and mRNA ISH using antibodies and probes (Harper et al., 1992) and compared the levels of IHC and ISH signals obtained with two types of fixation procedures, these being routine fixation and fixation using ultrasound. Furthermore, three different times were used in the routine method. The results show that ultrasound fixation provided even kappa immunoglobulin signal levels for both IHC and ISH which indicates that ultrasound can overcome fixed surface tissue which could otherwise act as a barrier to subsequent inward diffusion of fixatives. Use of ultrasound results in even fixation within the tissue blocks, and therefore results in even preservation of mRNAs. By contrast, as could be expected, 30 minutes or 6 hours of routine fixation did not allow any ISH signal, and 22 hours of routine fixation gave uneven results within the tissue blocks with better mRNA preservation in the periphery than in the center of the sections. However, the IHC results were not seriously affected by the routine fixation. This further indicates that with the routine fixation method formaldehyde inhibition of RNase activity is more difficult than preservation of antigen epitopes. These phenomena have been observed by other researchers using perfusion and immersion fixation (Tournier et al., 1987).

The methods disclosed herein describe a novel technique for rapidly preserving tissues for morphologic, biochemical and molecular studies. The ultrasound-mediated fixation and processing method allow preservation of high quality morphology, proteins and mRNA from routine formalin fixation and processing. The technique is fast, simple, easy to perform, and versatile. The ultrasound fixed and processed tissue may be used for rapid IHC or ISH or for rapid clinical pathology diagnosis. High quality fixed tissue sections may be used for laser capture microdissection, mRNA extraction and PCR studies. High quality fixed tissue blocks may be used for high-throughput tissue microarray analyses of the DNA, RNA and protein targets for a large series of cancer research. The techniques described can be applied not only to tissue sections but also to assays being performed on a membrane (e.g., Northerns, Southerns and Westerns), on DNA chips, or on any other type of microarray.

Examples are set out below which detail specifics for a variety of techniques including H & E staining, immunostaining, in situ hybridization of nucleic acid, and reverse transcription polymerase chain reaction. These methods, apart from their being combined with ultrasound treatment, are well known to those of skill in the art. The present invention is further detailed in the following Examples, which are offered by way of illustration and are not intended to limit the invention in any manner. Standard techniques spell known in the art or the techniques specifically described belong are utilized.

EXAMPLE 1

Tissue Fixation and Processing

A general procedure for preparing, tissue fixed by NBF, processed and imbedded in paraffin using ultrasound as part of the process to decrease the required time to prepare the sample for use follows. Specifics are set out in the Examples which follow the general procedure. Those of skill in the art recognize that many variations can be made in the following procedures and the values set forth in the following procedures and Examples are not meant to be limiting.

A) Fixation

Step 1: A fresh tissue sample is cut in a size range from 3 to 5 mm thick preferably less than 5 mm thick.

Step 2: The tissue sample (a single piece) is immersed in a 10% formalin solution or other acceptable fixative. Depending on the type of tissue, the sample is immersed from 5 to 30 minutes at 37° C. preferably for 15 minutes. During the immersion the sample is subjected to ultrasonic energy. When using a fixed power setting, the frequency of the ultrasonic waves to be used depends upon the thickness and size of the tissue and is a frequency in the range of 0.1-50 MHz. Frequencies toward the lower range are used for thick and large size tissue samples whereas thin and small sized samples use higher frequencies. When using a fixed frequency the power rating is adjusted according to a size and thickness of the tissue sample. Thick and large size tissues require use of higher power and thin and small size tissues use lower power. The nature of the tissue is also important with tough tissue (e.g., uterine tissue or ligament) requiring a lower frequency and higher intensity of ultrasound whereas soft tissue (e.g., fat, lung and liver) requires a higher frequency and looser intensity of ultrasound.

B) Processing

Step 3: Dehydration: The tissue is first immersed in an 80% to 95% alcohol solution for 1 to 10 minutes at 37° C. The time is dependent upon the type and size of tissues and is preferable in the range of 2.5-5 minutes at 37° C. During this step, the sample is subjected to ultrasonic energy at the same or different frequency and power (e.g., lower frequency and higher intensity) as used in Step 2. The sample is then immersed in a 100% alcohol solution for 1 to 15 minutes at 37° C. preferably 5-7 minutes at 37° C. During this step the sample is subjected to ultrasonic energy at the same or different frequency and power (e.g., lower frequency and higher intensity) as in Step 2.

Step 4: Clearing: The tissue sample is immersed in a xylene solution for 2 to 20 minutes at 37° C. The time is dependent upon the type and size of the tissue samples and is preferably 3 minutes at 37° C. During this step the sample is subjected to ultrasonic energy at the same or different frequency and power (e.g., lower frequency and higher intensity) as used in Step 2.

Step 5: Infiltration: The tissue sample is immersed in a paraffin solution for 2 to 20 minutes at 60° C. The time is dependent on the type and size of the tissue samples, preferably 10-15 minutes at 60° C. During this step the sample is subjected to ultrasonic energy at the same or different frequency and power (e.g., lower frequency and higher intensity) as used in Step 2.

C) Imbedding

Step 6: Imbedding: The tissue sample is imbedded in a paraffin block without use of ultrasound and cooled to −10 to −20° C.

D) Deparaffinization and hydration

During the following steps the tissue section sample is subjected to ultrasonic energy for less than 2 minutes at a higher single frequency setting and a lower power setting.

The tissue section sample is immersed in 4 changes of xylene solution for 10 seconds for each immersion. The tissue sample is immersed in two changes of 100% alcohol for 10 seconds for each immersion. The tissue sample is immersed in two changes of a 95% alcohol solution for 5 seconds for each immersion. The tissue sample is immersed in a 70% alcohol solution for 10 seconds. The tissue sample is washed with distilled water or phosphate buffered saline (PBS) for 10 seconds.

E) Dehydration

During this procedure the tissue sample is subjected to ultrasonic energy for a little longer than 1 minute.

The tissue sample is washed with distilled water for 10 seconds. The tissue sample is immersed in a 70% alcohol solution for 10 seconds. The tissue sample is immersed in two changes of a fresh 95% alcohol solution for 5 seconds for each immersion. The tissue sample is immersed in two changes of a fresh 100% alcohol solution for 10 seconds for each immersion. The tissue sample is immersed in two changes of a fresh xylene solution for 10 seconds for each immersion.

After imbedding a sample in paraffin and sectioning it, it can be used for a variety of techniques which are well known to those of skill in the art. One common procedure is staining of the tissue section. Hematoxylin and eosin (H & E) is the most common staining procedure used in pathology. Every case must have H & E staining for making a pathologic diagnosis. Deparaffinized tissue section slides which are in slide holders are placed vertically into a staining dish with 500 mL of hematoxylin solution for 10 seconds with ultrasound followed by washing with running tap water in a staining dish for 5 seconds with ultrasound. The slides are placed in 95% ethyl alcohol for 5 seconds with ultrasound and counterstained in eosin-phloxine solution for 10 seconds with ultrasound. The samples are dehydrated and cleared using two changes each of 95% ethyl alcohol, absolute ethyl alcohol, and xylene for less than one minute each in the presence of ultrasound. The ultrasound used throughout this procedure is in the range of 1-5 MHz and greater than 5 W/cm$^2$.

The tissue which has been fixed and mounted can be used for any one of several techniques such as staining, hybridization, etc. In performing these techniques ultrasound treatment can be used in the steps used for those treatments.

In performing ultrasound for postfixation treatments such as staining or hybridization, it is preferred that a specific frequency and power of ultrasound be utilized, although this will depend upon the exact tissue, size of the probe and treatment. It is preferred that each transducer has a single head, each putting out a single frequency wave. Each head can be a different frequency, preferably 1-5 MHz or 0.1-30 MHz. Using the prior art disclosure of 20 to 50 KHz results in undesirable effects and causes cavitation and destruction in tissue samples. Each tissue (fat, bone, etc.) requires a different frequency. The present invention allows the use of more power without destroying cells and therefore equates to greater speed of reaction. The method of the present invention yields much larger RNA strands with the use of the specific ultrasonic energy technique. Further, the present invention enables in situ hybridization and IHC results to be uniform throughout.

EXAMPLE 2

Ultrasonic Apparatus and Application

The ultrasonic apparatus used in the present study was specifically designed by the inventor and built by Bio-Quick, Silver Spring, Md. It consisted of an ultrasonic generator and a 1.6-1.7 MHz ceramic transducers (1.5 cm diameter) with adjustable output intensity range of 1 to 22 W/cm². The tissue (only one sliced tissue at time), which was irradiated by ultrasound in 200 mL of NBF, grades of alcohol, xylene and 60° C. paraffin was directly faced and aimed at the transducers. The distance between the transducers and irradiated tissue was within 3 cm to insure that the tissue received even and accurate ultrasound energy. The application of ultrasound was always continuous rather than pulsed. The tissue receiving ultrasound energy was monitored by means of a UW-3 ultrasound wattmeter (Bio-Tek Instruments Inc. Winooski, Vt.). The temperature of the fixative inside the container was limited to 37° C. during the exposure to ultrasound.

EXAMPLE 3

Immunohistochemistry with Ultrasound

Tissue sections from each experiment were stained with a panel of seven primary antibodies (CD20, CD45, CD3, CD5, Bcl-2, kappa and lambda: Table 1). The primary antibodies were demonstrated using the ABC method (Hsu et al., 1981; Chu et al., 1992) as follows: sections were deparaffinized and taken through to 70% alcohol before being placed into water. Sections were then pretreated with/without antigen retrieval by MW (Shi et al., 1991) or pepsin (Chu et al., 1999) as required for each antibody (Table 1). Sections were rinsed in phosphate buffered saline (PBS) and incubated in primary antibody, for 5-10 minutes at room temperature with a higher single frequency (1.6-1.7 MHz) setting and lower power (0.01-5 W/cm²) setting of ultrasound. After three rinses in PBS for 5 seconds with ultrasound, sections were incubated in biotinylated second antibody for 2.5 or 5 minutes at room temperature with ultrasound. Sections were rinsed in PBS with ultrasound and treated with 0.3% hydrogen peroxide for 1-2 minutes with ultrasound, followed by incubation in ABC complex for 2 or 5 minutes with ultrasound. Antibody binding sites were localized using 3,3'-diaminobenzidine for 10 seconds with ultrasound and sections were lightly counterstained with hematoxylin for 5 seconds with ultrasound. The ultrasound used throughout this Example was at 1.6-1.7 MHz and 0.01-5 W/cm². The exact values depended upon the specific antibody. A higher intensity was used for those that otherwise gave a higher background.

TABLE 1

| CD | Clone | Dilution | Pretreatment | Supplier |
|---|---|---|---|---|
| CD20/L26 | Mono | 1:400 | None | Dako |
| CD45/LCA | Mono | 1:250 | None | Dako |

TABLE 1-continued

| CD | Clone | Dilution | Pretreatment | Supplier |
|---|---|---|---|---|
| CD3 | Poly | 1:500 | Pepsin | Dako |
| CD5/4C7 | Mono | 1:100 | Microwave | Novocastra |
| Bcl-2 | Mono | 1:100 | Microwave | Dako |
| Kappa | Poly | 1:50.000 | Pepsin | Dako |
| Lambda | Poly | 1:100.000 | Pepsin | Dako |

EXAMPLE 4

In Situ Hybridization with Ultrasound

Tissue sections were deparaffinized and prepared with enzymatic or MW antigen retrieval pretreatment before hybridization. A synthetic oligonucleotide probe directed against pole A mRNA and a probe for mRNA of kappa immunoglobulin were labeled with fluorescein isothiocyanate (FITC) (sequences provided by BioGenex, San Ramon Calif.). FITC-labeled probe was applied to the tissue sections which were then coverslipped and denatured at 100° C. for 5 minutes in a vegetable steamer. The slides were cooled down and hybridized in the presence of ultrasound at a high single frequency with a low power setting at room temperature for 10-60 minutes in the steamer. Sections were washed twice, 3 seconds each, in 2X SSC with ultrasound and then incubated for 10 minutes with monoclonal mouse anti-FITC with ultrasound, followed by two washes in PBS with ultrasound, 3 seconds each. Biotinylated secondary antibody was incubated with the tissue sections in the presence of ultrasound for 2-5 minutes at room temperature, followed by two 3 second washes in PBS with ultrasound Streptavidin-biotinylated peroxidase and 5-bromo-4-chloro-3-indolyl phosphate/nitroblue tetrazolium (BCIP/NBT) reagents were used in the presence of ultrasound. The ultrasound used throughout this Example was at 1.6-1.7 MHz and 0.01-5 W/cm². The intensity used depended upon the probe length with a higher power being used with longer probes.

EXAMPLE 5

Northern and Southern Hybridization with Ultrasound

Experiments were performed just as in Example 4 except that the experiments were performed with the nucleic acid bound to a membrane rather than being in situ.

EXAMPLE 6

Robotic System

Figure 7:
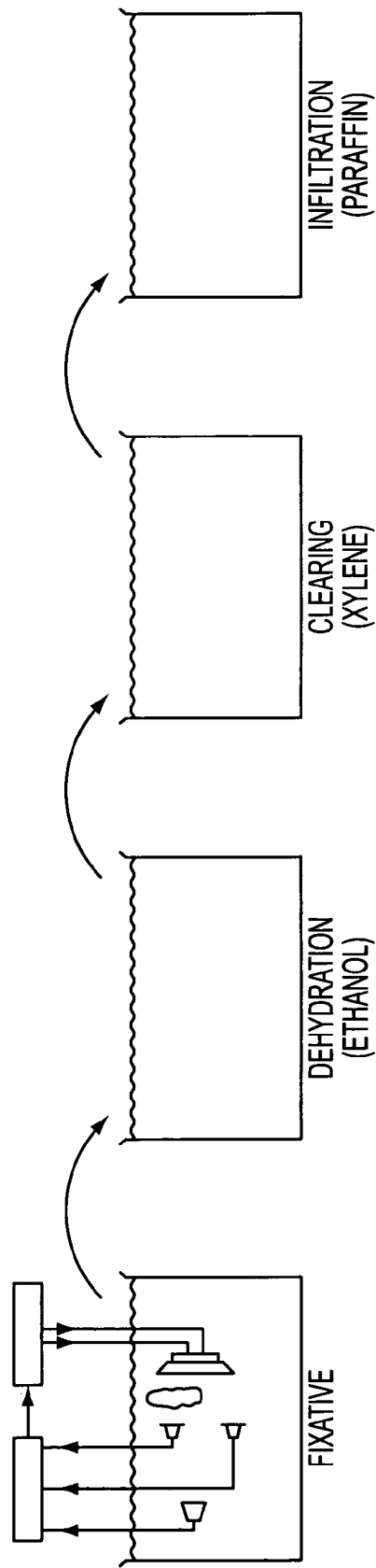
FIG. 7 represents a system shoring four solutions, each in a different container. The complete system of tissue, ultrasound generator, transducer, sensors and CPU can be moved from one container to the next. This is preferably controlled by a robotic system which is not shown.

In this system, illustrated in FIG. 7 the tissue sample as well as the transducer and sensors are moved from one reaction chamber to the next. To fix a tissue sample, the tissue, transducer and sensors are all placed into a first reaction chamber containing fixative. After treatment with ultrasound in the fixative, a robotic system removes the tissue sample, transducer and sensors and moves them all to the next reaction chamber containing ethanol. After treatment with ultrasound in the ethanol is complete, the robotic system moves the tissue, transducer and sensors to a reaction chamber containing xylene. After treatment is complete in the xylene, the robotic system moves the tissue into a reaction chamber containing paraffin at 60° C. The CPU is programmed to control the ultrasound generator for each of these steps. Once the tissue is imbedded with paraffin, the fixed tissue is robotically removed from the reaction chamber and surrounded with more paraffin to create a paraffin block.

EXAMPLE 7

Auto-Fixation and Processing Reactor

In Example 6, a robotic system was used to move the sample, transducer and sensors from one solution to the next throughout the fixation process. In this Example, illustrated in FIG. 8, the tissue, transducer and sensors remain fixed and the solutions are changed. The tissue is placed in a reaction chamber through which fluids can be pumped. Cleans for heating and/or cooling the reaction chamber are also illustrated. Fluid or reagent is pumped into the reaction chamber and ultrasound is produced by the transducer. The sensors monitor the reaction and feedback through the CPU to control the ultrasound generator. When reaction with one fluid is complete, the fluid is pumped out as the next fluid or reagent is pumped in. A distributor selects which fluid, or air or gas if desired, is pumped in. The used fluid is pumped out to a waste receptacle or can be recycled if desired. Flow of fluids and reagents through the reaction chamber can be continuous with a distributor, controlled by the CPU, changing which fluid/reagent enters the chamber. Alternatively flow can be pulsed such that the chamber is filled, flow is stopped or circulated as the reaction occurs, and then flow begins again with the next reagent/fluid after the reaction has finished. After the paraffin is imbedded, the chamber will cool to −10 to −20° C., a paraffin block is formed and is reads to be cut.

EXAMPLE 8

Auto Reaction with a Membrane

This system is nearly identical to that of Example 9 except that in place of a tissue sample a membrane with bound sample (e.g., nucleic acid or protein) is placed into the reaction chamber. This can be used for Northern, Southern and Western blots, ELISA, etc. Furthermore, in place of a membrane, a chip such as a DNA chip or an immuno chip can be used.

EXAMPLE 9

Automated Immunohistochemistry

This system is very similar to that of Example 7. Here a slide with a tissue sample mounted on it is used in place of a tissue or a tissue section in a reaction chamber. As illustrated (FIG. 9) the tissue is below the slide and above the transducer with a channel between the slide and the transducer. Heating and cooling elements can also be included. Solutions and reagents are passed through the channel such that thee contact the tissue sample. The extent of reaction in the presence of ultrasound treatment is measured by time or, if sensors are present, by feedback from the sensors. As each reaction is completed a change of solution/reagents occurs. Each fluid is pumped to a waste receptacle or recycled.

EXAMPLE 10

Automated In Situ Hybridization

This system is very similar to that of Example 9 except that in situ hybridization is performed rather than immunohistochemistry.

EXAMPLE 11

In Situ PCR Hybridization

This Example uses a setup very similar to that described in Example 9. The difference is an added pump which can be used to remove samples of amplification fluid as the amplification is occurring. This is shown in FIG. 9. If desired, this added pump can deliver sample to a gel. This can be performed at time points during the amplification if desired or simply at the end of a specified time period. As the in situ PCR (polymerase chain reaction) is occurring, amplification occurs in the presence of ultrasound and then hybridization occurs to nucleic acid within the cells of the tissue. Some of the amplified product stays in place in the cells, but a large percentage of amplified product washes off the tissue and into the solution. By sampling the solution it is possible to determine whether the in situ PCR is working properly by measuring the size of the products being formed. If it does work properly then the amplified nucleic acid product will appear in the solution. Samples of the solution can be run on a gel and stained or autoradiographed to determine if a band of nucleic acid of the expected size has been produced. If the desired band is seen, the PCR has worked and it is worth continuing the workup of the in situ hybridization. If no band is seen on the gel then no amplification occurred and further workup of the in situ hybridization will not be performed.

While the intention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Azumi N. Joyce J, and Battifora H (1990). "Does rapid microwave fixation improve immunohistochemistry?" *Mod. Pathol* 3:368.

Baker J R (1959). *Principles of biological microtechnique: a study of fixation and dyein.* New York, Barnes & Noble. Inc.

Ben-ezra J., Johnson D A, Rossi J, Cook N, and Wu A (1991). "Effect of fixation on the amplification of nucleic acids from paraffin-embedded material by the polymerase chain reaction." *J Histochem. Cytochem.* 39:351.

Bernard G (1974), "Microwave irradiation as a generator of heat for histological fixation." *Stain Technol* 49:215.

Bonner R F, Emmert-Buck M. Cole K, Pohida T, Chuaqui R, Goldstein S, and Liotta L A (1997). "Laser capture microdissection: molecular analysis of tissue." *Science* 278:1481, 1483.

Boon M E, Kok L P, and Ouwerkerk-Noordam E (1986). "Microwave-stimulated diffusion for fast processing of tissue: reduced dehydrating, clearing, and impregnating times," *Histopathology* 10:303.

Botsman N E and Bobrova G G (1968). ["An accelerated method of making histological preparations with the use of ultrasonics"]. *Arkh Patol* 30:72.

Brandzaeg P (1982). "Tissue preparation methods for immunocytochemistry", in Bullock G R and Petrusz P (eds): *Techniques in immunocytochemistry*, New York, Academic Press, p. 1.

Chu W S, Abbondanzo S L, and Frizzera G (1992). "Inconsistency of the immunophenotype of Reed-Sternberg cells in simultaneous and consecutive specimens from the same patients." *Am J. Pathol.* 141:11.

Chu W S, Aguilera N S I, Wei M Q, and Abbondanzo S L (1999), "Anti-apoptotic marker, Bcl-XL, expression on Reed-Sternberg cells of Hodgkin's disease using a novel monoclonal marker. YTH-2H12." *Hum Pathol* (in press).

DeRisi J, Penland L, Brown P O, Bittner M L, Meltzer P S, Ray M, Chen Y, Su Y A, and Trent J M (1996). "Use of a cDNA microarray to analyse gene expression patterns in human cancer [see comments]." *Nat. Genet.* 14:457.

Drakhli E I (1967). ["Methods of using ultrasonics in a quick histological treatment of tissues"]. *Arkh. Patol* 29:81.

Drury R A B and Wallington E A (1980). *Carleton's histological technique.* Oxford, Oxford University Press.

Emmert-Buck M R, Bonner R F, Smith P D, Chuaqui R F, Zhuang Z, Goldstein S R, Weiss R A, and Liotta L A (1996). Laser capture microdissection [see comments]. *Science* 274:998.

Fend F, Emmert-Buck M R, Chuaqui R, Cole K, Lee J, Liotta L A, and Raffeld M (1999a). "Immuno-LCM: laser capture microdissection of immunostained frozen sections for mRNA analysis." *Am J. Pathol.* 154:61.

Fend F, Quintanilla-Martinez L, Kumar S, Beaty M W, Blum L, Sorbara L, Jaffe E S, and Raffeld M (1999b). "Composite low grade B-cell lymphomas with two immunophenotypically distinct cell populations are true biclonal lymphomas: A molecular analysis using laser capture microdissection [In Process Citation]." *Am J Pathol* 154:1857.

Foss R D, Guha-Thakurta N, Conran R M, and Gutman P (1994). "Effects of fixative and fixation time on the extraction and polymerase chain reaction amplification of RNA from paraffin-embedded tissue: comparison of two housekeeping gene mRNA controls." *Diagn. Mol Pathol* 3:148.

Fox C H, Johnson F B, Whiting J, and Roller P P (1985). "Formaldehyde fixation." *J. Histochem. Cytochem* 33:845.

Goldsworthy S, Stockton P S, Trempus C S, Foley J, and Moronpot R R (1999). "Effects of fixation on RNA extraction and amplification from laser capture microdissected tissue." *Mol. Carcinog.* 25:86.

Harper S J, Pringle J H, Gillies A, Allen A C, Layward L, Feehally J, and Lauder I (1992). "Simultaneous in situ hybridisation of native mRNA and immunoglobulin detection by conventional immunofluorescence in paraffin was embedded sections." *J. Clin. Pathol.* 45:114.

Hsu S M, Raine L, and Fanger H (1981). "The use of avidine-biotin-peroxidase complex (ABC) in immunoperoxidase techniques a comparison: between ABC and unlabeled antibody (PAP) procedures." *J Histochem Cytochem.* 29:577.

Kononen J, Bubendorf L, Kallioniemi A, Barlund M, Schraml P, Leighton S, Torhorst J, Mihatsch M J, Sauter G, and Kallioniemi O P (1998). "Tissue microarrays for high-throughput molecular profiling of tumor specimens [see comments]." *Nat. Med* 4:844.

Krafft A E, Duncan B W, Bijwaard K E, Taubenberger J K, and Lichy J H (1997). "Optimization of the isolation and amplification of RNA from formalin-fixed, paraffine-embedded tissue: the Armed Forces Institute of Pathology experience and literature review." *Molecular Diagnosis* 2:217.

Login G R (1978). "Microwave fixation versus formalin fixation of surgical and autopsy tissue." *Am. J. Technol* 44:435.

Login G R (1998). "The need for clinical laboratory standards for microwave-accelerated procedures." *J Histotechnol* 21:7.

Login G R and Dvorak A M (1985). "Microwave energy fixation for electron microscopy." *Am. J. Pathol.* 120:230.

Login G R, Schnitt S J, and Dvorak A M (1987). "Rapid microwave fixation of human tissues for light microscopic immunoperoxidase identification of diagnostically useful antigens" *Lab. Invest.* 57:585.

Mayers C P (1970). "Histological fixation by microwave heating." *J Clin. Pathol.* 23:273.

Miller D L (1991). "Update on safety of diagnostic ultrasonography." *J Clin Ultrasound* 19:531.

Miller K, Auld J, and Jessup E (1995). "Antigen unmasking on formalin-fixed routinely-processed paraffin was-embedded sections by pressure cooking: A comparison with microwave oven heating and traditional methods." *Advances in Anatomic Pathology* 2:60.

Miller M W, Miller D L, and Brayman A A (1996). "A review of in vitro bioeffects of inertial ultrasonic cavitation from a mechanistic perspective." *Ultrasound in Med & Biol.* 22:1131.

Norton A J, Jordan S, and Yeomans P (1994). "Brief, high-temperature heat denaturation (pressure cooking): a simple and effective method of antigen retrieval for routinely processed tissues." *J. Pathol.* 173:371.

Nuovo G J and Richart R M (1989). "Buffered formalin is the superior fixative for the detection of HPV DNA by in situ hybridization analysis." *Am J Pathol* 134:837.

Obertyshev V G (1987). ["Ultrasonic express paraffin handling of histological specimens"]. *Sud. Med. Ekspert* 30:56.

Polonyi J, Sadlonova Z, and Slovakova D (1984). ["Use of ultrasound to hasten glutaraldehyde fixation of animal tissues for electron microscopy"]. *Bratisl Lek. Listy.* 81:566.

Robb I A, Carpenter B F, and Jimenez C L (1991). "Rapid ultrasonic bath processing for electron microscopy." *Ultrastruct. Pathol.* 15:83.

Rozenberg V D (1991). ["The results and prospects of using ultrasound in pathohistological practice"]. *Arkh. Patol* 53:68.

Sambrook J, et al. (1989). *Molecular Cloning: A Laboratory Manual,* 2nd Ed. (Cold Spring Harbor Laboratory, Cold Spring Harbor. N.Y.).

Schena M, Shalon D, Davis R W, and Brown P O (1995). "Quantitative monitoring of gene expression patterns with a complementary DNA microarray [see comments]." *Science* 270:467.

Shi S R, Key M E, and Kalra K L (1991). "Antigen retrieval in formalin-fixed paraffin-embedded tissues: An enhancement method for immunohistochemical staining based on microwave oven heating of tissue sections." *J. Histochem. Cytochem.* 39:741.

Shmurun R I (1992). ["Methods for the rapid preparation of paraffin blocks"]. *Arkh Patol.* 54:46.

Taylor C R (1986). "Immunomicroscopy: a diagnostic tool for the surgical pathologist", in Anonymous, Philadelphia, W. B. Saunders, p. 43.

Taubenberger J K, Reid A H, Krafft A E, Bijwaard K F and Fanning T G (1997). "Initial genetic characterization of the 1918 "Spanish" Influenza virus." *Science* 275: 1793.

Tournier I, Bernuau D, Poliard A, Schoevaert D, and Feldmann G (1987) "Detection of albumin mRNAs in rat liver by in situ hybridization: usefulness of paraffin embedding and comparison of various fixation procedures." *J. Histochem Cytochem.* 35:453.

Visinoni F, Milios J, Leong A S, Boon M E, Kok L P, and Malcangi F (1998). "Ultra-rapid microwave/variable pressure-induced histoprocessing: description of a new tissue processor." *J. Histotechnol* 21:219.

Weiss L M and Chen Y Y (1991). "Effects of different fixatives on detection of nucleic acids from paraffin-embedded tissues by in situ hybridization using oligonucleotide probes." *J. Histochem Cytochem* 39:1237.

Williams J H, Mepham B L, and Wright D H (1997). "Tissue preparation for immunocytochemistry." *J Clin Pathol.* 50:422.

Yasuda K, Yamahita S, Shiozawa M, Aiso S, and Yasui Y (1992). "Application of ultrasound for tissue fixation: combined use with microwave to enhance the effect of chemical fixation." *Acta Histochem Cytochem* 25:237.

What is claimed is:

1. A system for fixing tissue samples, comprising:
    a reaction chamber including a solution selected from the group consisting of a fixative, alcohol, xylene and paraffin for immersing a tissue sample therein;
    an ultrasound transducer, immersed in said solution, to irradiate the tissue sample, immersed in said solution, with ultrasound energy, wherein said ultrasound transducer is within 2 inches of said tissue sample;
    an ultrasound generator, coupled to the ultrasound transducer, to generate the ultrasound energy;
    at least one sensor, immersed in the solution, to monitor at least one of a physical parameter of the tissue sample and the ultrasound energy selected from the group consisting of temperature, size, tissue type, tissue density, ultrasound frequency, and ultrasound intensity; and
    a central processing unit, coupled to the ultrasound generator and the sensor, programmed to control the ultrasound generator and to adjust at least one of a frequency between 100 kHz and 50 MHz and an intensity between 0.01 and 200 W/cm2 of the ultrasound energy that is applied to the tissue sample in response to a signal received from the sensor, in order to fix the tissue sample in the solution with no or minimal damage.

2. The system of claim 1, wherein said at least one sensor is selected from the group consisting of an ultrasound sensor, and an infrared temperature sensor.

3. The system of claim 1 wherein said at least one sensor produces signals which are processed by the central processing unit.

4. The system of claim 1 wherein the transducer generates ultrasound of a frequency of at least 100 KHz.

5. The system of claim 4 wherein the transducer generates ultrasound of a single frequency or of multiple frequencies in the range 100 KHz to 50 MHZ.

6. The system of claim 1 wherein the ultrasound transducer produces ultrasound of a power in the range of 0.01-200 W/cm$^2$.

7. The system of claim 1 wherein the solution is a solution of 10% formalin.

8. The system of claim 1 wherein the solution is alcohol to dehydrate the tissue sample.

9. The system of claim 1 wherein the solution is xylene.

10. The system of claim 1 wherein the solution is paraffin.

11. The system of claim 1 further comprising a first pump and a second pump, wherein the first pump pumps a second solution into the reaction chamber and the second pump pumps a first solution out of the reaction chamber.

12. A system for fixing tissue samples, comprising:
    a reaction chamber including a solution selected from the group consisting of a fixing agent, a dehydrating agent, a clearing agent and paraffin for immersing a tissue sample therein;
    an ultrasound transducer, immersed in said solution, to irradiate the tissue sample, immersed in said solution, with ultrasound energy of at least 100 KHz and a power in the range of 0.01-200 W/cm$^2$, wherein said ultrasound transducer is within 2 inches of said tissue sample;
    an ultrasound generator, coupled to the ultrasound transducer, to generate the ultrasound energy;
    at least one sensor, immersed in the solution, to monitor at least one of a physical parameter of the tissue sample and the ultrasound energy selected from the group consisting of temperature, size, tissue type, tissue density, ultrasound frequency, and ultrasound intensity; and
    a central processing unit, coupled to the ultrasound generator and the sensor, programmed to control the ultrasound generator and to adjust at least one of a frequency between 100 kHz and 50 MHz and an intensity between 0.01 and 200 W/cm2 of the ultrasound energy in response to a signal received from the sensor, in order to fix the tissue sample in the solution with no or minimal damage.

13. The system of claim 12, wherein the transducer generates ultrasound of a single frequency or of multiple frequencies in the range 100 KHz to 50 MHZ.

14. The system of claim 13, wherein said at least one sensor is selected from the group consisting of an ultrasound sensor, and an infrared temperature sensor.

15. The system of claim 13, wherein said at least one sensor produces signals which are processed by the central processing unit.

16. The system of claim 13 further comprising a first pump and a second pump, wherein the first pump pumps a second solution into the reaction chamber and the second pump pumps a first solution out of the reaction chamber.

17. The system of claim 4, wherein the transducer generates ultrasound of a single frequency or of multiple frequencies in the range 100 KHz to 1 MHZ.

18. The system of claim 12, wherein the transducer generates ultrasound of a single frequency or of multiple frequencies in the range 100 KHz to 1 MHZ.

19. The system of claim 1, wherein the transducer includes multiple heads.

20. The system of claim 1, wherein the transducer revolves around the tissue sample.

21. The system of claim 1, wherein the tissue sample rotates.

22. The system of claim 12, wherein the transducer includes multiple heads.

23. The system of claim 12, wherein the transducer revolves around the tissue sample.

24. The system of claim 12, wherein the tissue sample rotates.

* * * * *